Figure 1:
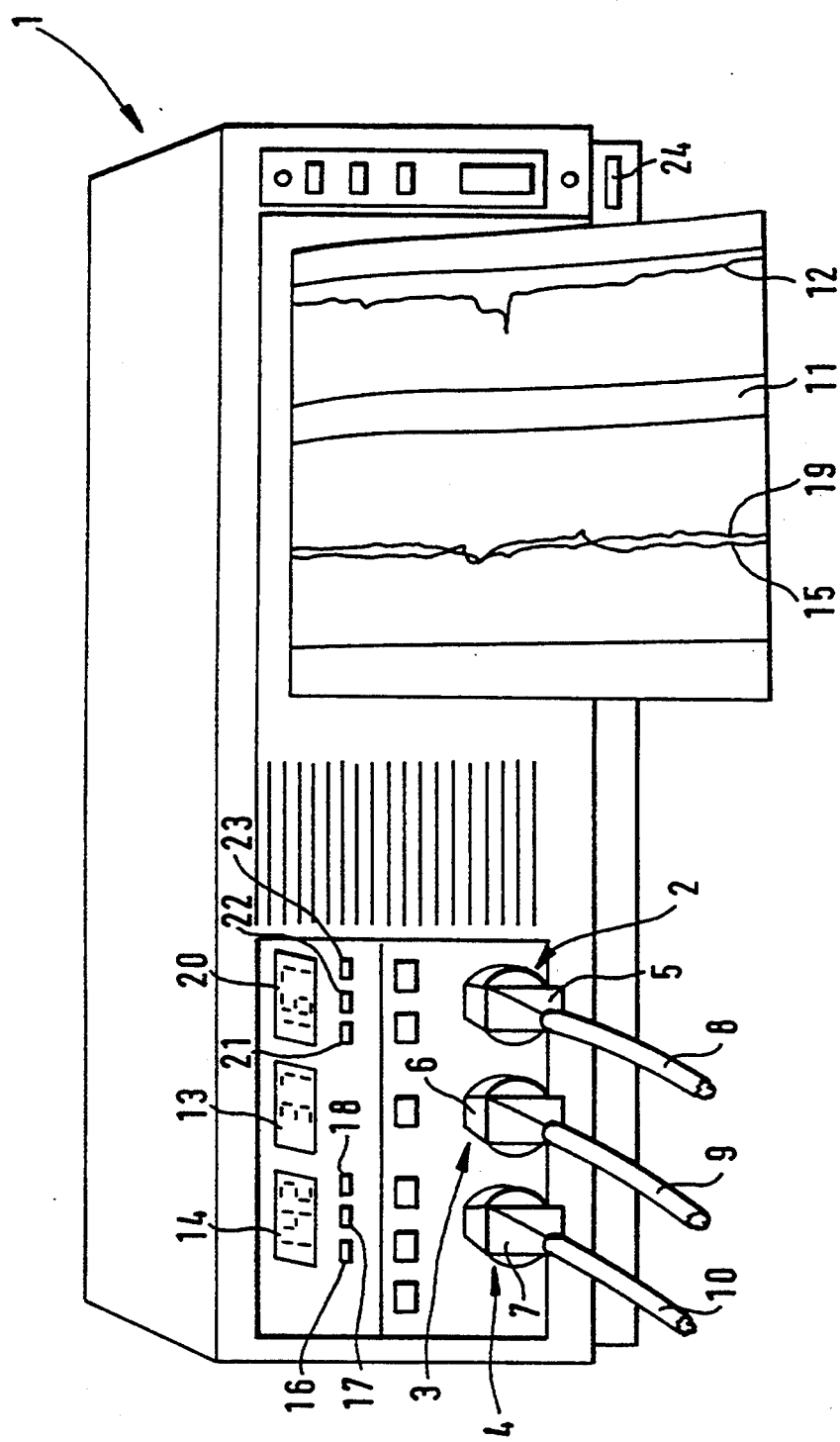

United States Patent [19]

Secker et al.

[11] Patent Number: 5,442,940
[45] Date of Patent: Aug. 22, 1995

[54] APPARATUS AND METHOD FOR EVALUATING THE FETAL CONDITION

[75] Inventors: Herbert Secker, Stuttgart; Guenter Hornung, Simmozheim; Friedemann Ulmer, Gaeufelden; Zoltan Takacs, Rottenburg; Andreas Herrmann, Dielheim, all of Germany

[73] Assignee: Hewlett-Packard Company, Palo Alto, Calif.

[21] Appl. No.: 78,327

[22] PCT Filed: Oct. 24, 1991

[86] PCT No.: PCT/EP91/02020

§ 371 Date: Jun. 22, 1993

§ 102(e) Date: Jun. 22, 1993

[87] PCT Pub. No.: WO93/08534

PCT Pub. Date: Apr. 29, 1993

[51] Int. Cl.[6] .............................................. A61B 5/02
[52] U.S. Cl. ........................ 128/670; 128/698; 128/661.07; 128/775; 304/413.03
[58] Field of Search ..................... 128/670, 903, 904, 661.07–661.1, 128/662.04, 698, 776; 364/413.03

[56] References Cited

U.S. PATENT DOCUMENTS 5,069,218  12/1991  Ikeda ................................. 128/670
5,123,420  6/1992   Paret ................................. 128/698
5,257,627  11/1993  Rapoport ....................... 128/661.07

OTHER PUBLICATIONS

"Development of and viser system for fuetal diagnosis during labor", A. Alonso et al., *Proc. of the Annual International Conference of the IEEE Engineering in Medicine Biology*, vol. 10.1 1355–1357, 4 Nov. 1989.

Karakas et al., "A nueral net learning algorithm for design of cardiatocograph signal evaluation expert system: Mydearbaby 90/2.47", *Proc. of Database and Expert Systems Applications*, 29 Aug. 1990 pp. 427–431.

Karnas et al., "Expert Systems for Evaluating Fetal Monitoring Signals," *Proc. of the ISCIS III, Nova Science Publication, NY; US.* 29 Oct. 1989, 317–322.

Arcay et al., "Physical and Functional Integration System for Intelligent Processing and Priorization of Variables in an ICU" *Proc. of the Annual Conference of the IEEE Engineers in Medicine Biology*, vol. 11 pp. 1993–1994, Nov. 9, 1989.

*Primary Examiner*—Lee S. Cohen
*Assistant Examiner*—Robert L. Nasser, Jr.

[57] ABSTRACT

An apparatus for evaluating the fetal condition prior to or under birth receives the signals of a fetal heart rate transducer and a toco transducer. The signals are first preprocessed in the time domain and in the frequency domain. A trace processor identifies possible events like decelerations and contractions. These are validated by a validation processor, whose output is then classified by a classification processor. A score processor scores the events and cooperates with an alarm handler and a reasoning processor. The rules according to which these processors operate are stored in a rule memory and may be edited or selected, or new rules may be set up, by a display or personal computer under control of an expert interface.

37 Claims, 23 Drawing Sheets

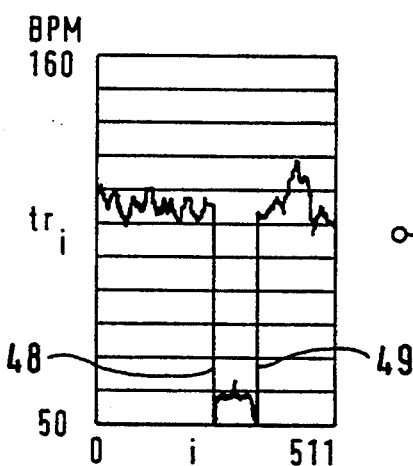
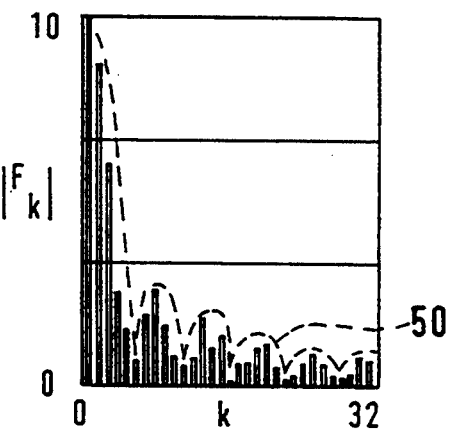
FIG. 6a              FIG. 6b
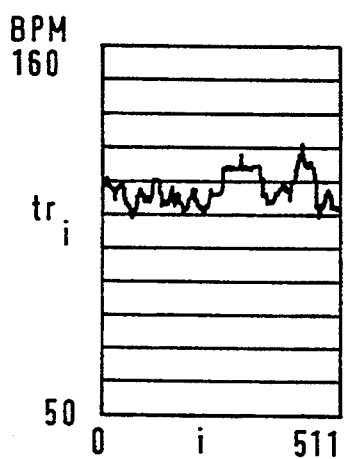
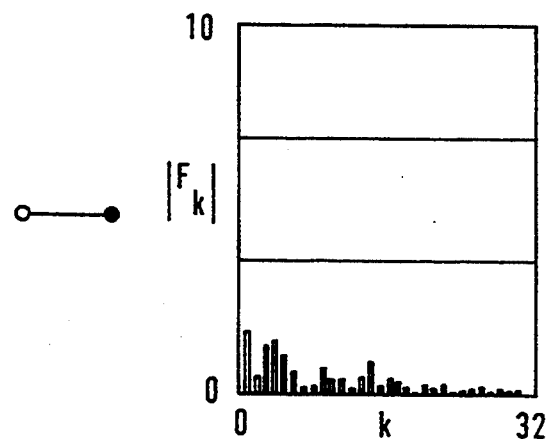
FIG. 7a              FIG. 7b

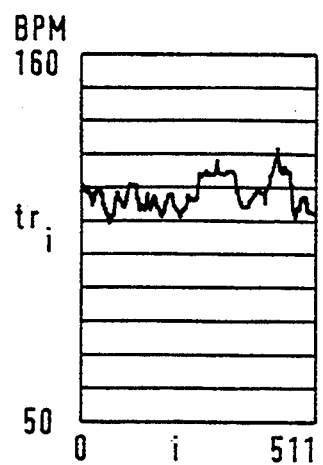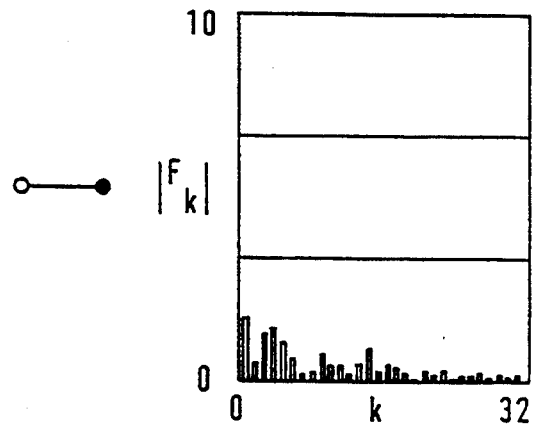
FIG.8a  FIG.8b
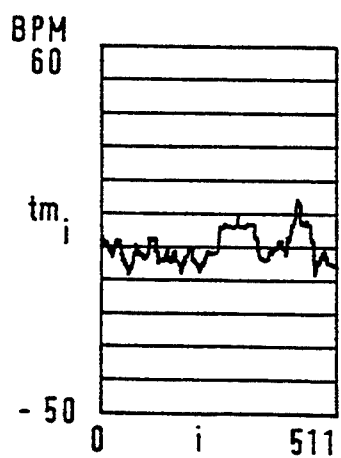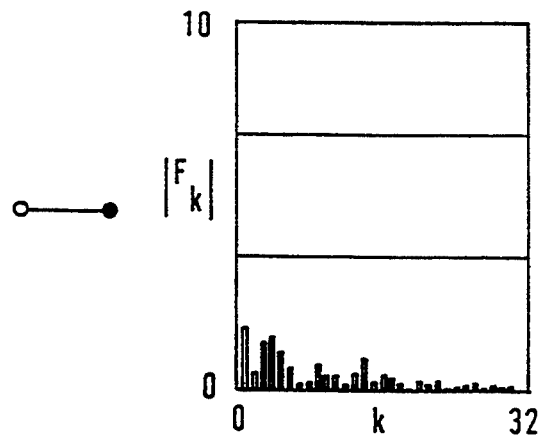
FIG.9a  FIG.9b

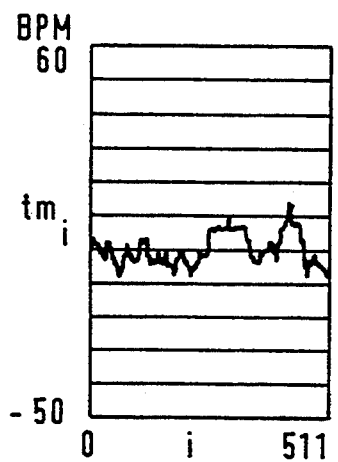 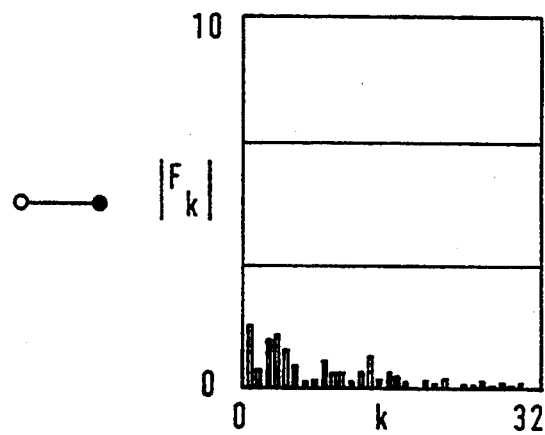
FIG.10a   FIG.10b
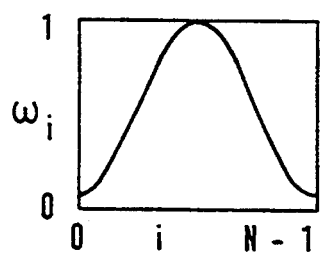 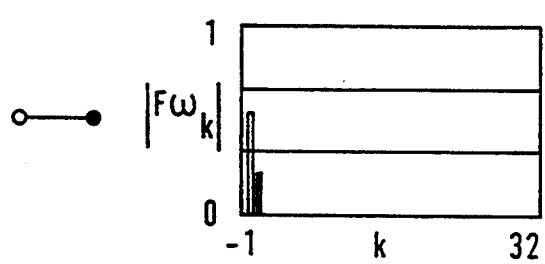
FIG.11a   FIG.11b
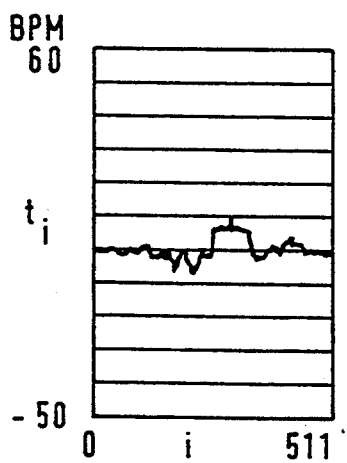 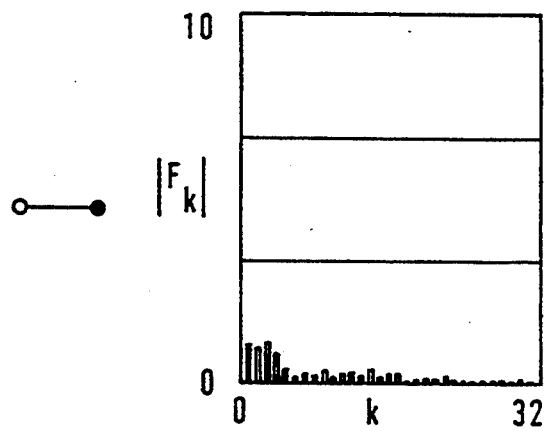
FIG.12a   FIG.12b

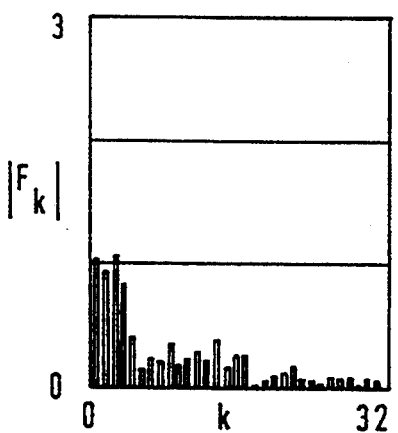
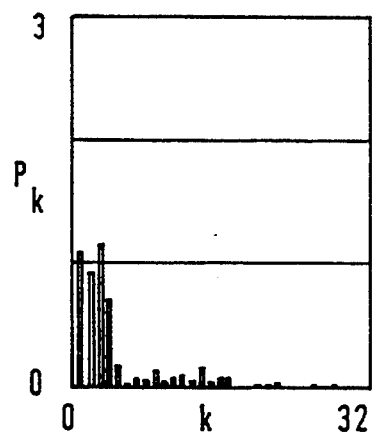
FIG.13a    FIG.13b
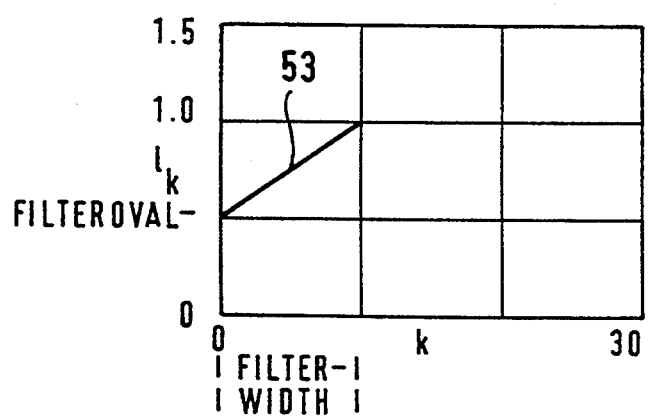
FIG.14
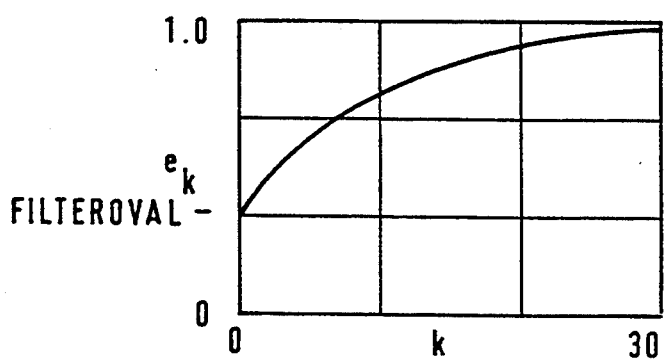
FIG.15

|  | NORMAL | ADD | PREPATHOLOGICAL | ADD | PATHOLOGICAL | ADD |
|---|---|---|---|---|---|---|
| BASELINE LEVEL | 120≤BL≤160 | 0 | 100≤BL<120 | 1 | <100 BPM | 4 |
|  |  |  | 160<BL≤180 | 1 | >180 BPM | 2 |
| NUMBER OF ACCELER-ATIONS | ≥3 | -1 | 0 | 2 |  |  |
| NUMBER OF LATE DECELERATIONS WITH AMPLITUDE >60 BPM | 0 | 0 | 1 | 1 | 3 | 4 |
| AMPLITUDE OF BASE-LINE VARIABILITY | 12≤AMP≤20 BPM | -2 | 20<AMP≤25 | 0 | >25 BPM | 2 |
|  |  |  | 5≤AMP<12 | 1 | <5 OSC/MIN | 3 |
| FREQUENCY OF BASELINE VARIABILITY | 3≤OSC≤5 | 0 | 1≤OSC<3 | 1 | <1 OSC/MIN | 3 |
|  |  |  | 5<OSC≤7 | 1 | >7 OSC/MIN | 3 |
| SUM-SCORE: | 0.2 |  | 3.5 |  | >5 |  |

FIG.19

APPARATUS AND METHOD FOR EVALUATING THE FETAL CONDITION

The present invention relates to an apparatus for evaluating the fetal condition prior to or under birth comprising first detection means for detecting the fetal heart rate from a first signal indicative of said fetal heart rate and generating a fetal heart rate trace; second detection means for detecting maternal labour from a second signal indicative of said maternal labour and generating a toco trace; processing means for evaluating said fetal heart rate trace and said toco trace, said processing means generating quantities representative of possible diagnostic information; and rule based operating means for extracting, validating, classifying or scoring said quantities or derived parameters, or said fetal heart rate trace or said toco trace. It also relates to a corresponding method for evaluating the fetal condition.

In gynecology and obstetrics, two medical parameters are important to assess the condition of the fetus. These parameters are the fetal beat-to-beat heart rate and uterus (or labour) activity. Simultaneous assessment of the fetal heart rate (FHR) and uterus activity (TOCO) allows determination of the fetal condition. Monitors measuring and recording both parameters are called fetal monitors or cardiotocographs (CTG monitors).

To obtain a signal indicative of the fetal heart rate, a so-called fetal scalp electrode may be applied to the fetal skin. These electrodes are usually spiral electrodes which are screwed into the fetal epidermis, see for example U.S. Pat. No. 3,827,428. Such direct electrodes allow very accurate measurements due to the excellent signal quality. Unfortunately, the internal or direct measurement can only be used after rupture of the membranes. Prior to that point in time (in particular, during gestation), indirect methods have to be used. These indirect measurements are performed abdominally, e.g. by listening the fetal heart sound or by measuring the Doppler shift of an ultrasound wave reflected by the moving parts of the fetal heart, particularly the heart walls and/or the heart valves. Further methods for recording the fetal heart rate are the abdominal electrocardiogram (recorded with electrocardiogram electrodes placed on the abdomen of the mother), the registration of fetal heart sounds with a microphone ("Phono") and the like. The present invention relates to all of these signals.

However, neither the electrocardiogram (in the case of a spiral electrode), nor the received ultrasound signal (in the case of an ultrasound transducer), nor any other signal indicative of the fetal heart beat, are of major diagnostic importance. What is in fact required to assess the fetal condition is the beat-to-beat heart rate. This means that heart beats have to be detected in the above signals and that the heart rate is calculated as the inverse of the time interval between two consecutive beats, i.e. the heart rate is calculated from beat to beat. This gives quite accurate information particularly on high-frequency variations in the fetal heart rate trace, which in turn is important for diagnosis.

Uterus activity, on the other hand, may be measured—in the antepartum phase—by means of an external toco transducer (tocodynamometer) placed externally on the fundus uteri of the mother, i.e. approximately centrally on the abdomen. Such toco transducer is a tension-measuring device, most commonly one or more resistive wire strain(s). The theory of what is really measured by these transducers is complex as uterus "hardness" as well as uterus deformation (and sometimes also respiration) influence the tension, but still it is possible to obtain clinically meaningful results, i.e. to discover frequency, amplitude and shape of a contraction.

After rupture of the membranes, an intravaginal toco transducer may be used, which is essentially a hose connected with a direct pressure transducer and introduced into the uterus. This second transducer generates very accurate and reliable readings.

Stand-alone fetal monitors usually record the fetal heart rate and TOCO time traces on paper, most commonly on a built-in stripchart recorder. It is also possible to transmit the related data to a host station, e.g. a central station, and retrieve them on a display like a CRT (cathode ray tube), or store them on magnetic media. The combined time traces of fetal heart rate and maternal labour (TOCO) will be called "cardiotocogram" (CTG) hereinafter.

Interpretation of the CTG, i.e. establishing a diagnosis on the basis of information provided by the CTG, is a critical and sensitive process. Some major reasons therefor are:

1. The fetal heart rate trace may contain a multiplicity of different patterns of diagnostic importance;
2. the diagnostic meaning of these patterns depends on their spectral components, i.e. a certain pattern in a given spectral range may have another meaning if it appears in another spectral range;
3. likewise, the diagnostic meaning of a pattern depends on how frequent it appears in the CTG—for example, a so-called "Dip 0" pattern is uncritical if appearing not more frequently than once per 15 minutes, but may raise concerns if appearing more frequently;
4. the interrelation between the fetal heart rate trace and the TOCO channel is of importance—for example, a deceleration (reduction of frequency) in the fetal heart rate channel which is delayed with respect to a contraction in the TOCO channel has a completely different meaning than a deceleration occurring simultaneously with a contraction;
5. the degree of events (i.e., strong versus small) is of importance.

Therefore, the assessment of the CTG is very sensitive to misinterpretation. On the other hand, a false or incomplete diagnosis may seriously endanger the fetus and/or the mother—misunderstanding of a CTG pattern indicating fetal oxygen deficiency, and therefore the need of appropriate therapy, could e.g. lead to cerebral injury of the fetus.

In order to prevent against the serious consequences of CTG misinterpretation, there have been several attempts to "formalize" the process of CTG interpretation. So-called "score tables" list several criteria or patterns which may appear in the CTG and assign a "score" or "points" (usually, an integer or a natural number) to the listed criteria or patterns. By addition of the single scores, one obtains a so-called "sum-score" (in another nomenclature, the "points" are added to obtain a "score", i.e. the term "score" already stands for the sum in this alternate nomenclature). A reference table relates the "sum-score" directly to the diagnostic assessment; for example, a sum-score equal to or exceeding 8 may be classified as "pathologic", whereas a sum-score equal to or exceeding 5 (but smaller than 8) may be classified as "prepathologic". A pathologic sum-score indicates high danger for the fetus and will usually result in a Caesarean Section. Prepathologic assessment indicates that increased attention is necessary, accompanied by additional therapeutic measures. On the other hand, in the given example, a sum-score below 5 stands for a harmless or "normal" diagnosis.

There are several "score tables" known in the art, for example the "Hammacher" score, the "Fischer" score and the like. These score tables have been developed by individual physicians. Their score tables differ slightly in their diagnostic focus and the way the calculations are made. Application of either of these score tables in clinical practice depends on the specific needs and experiences of the hospital and the attending physician.

Although these score tables make CTG assessment more consistent (e.g. if CTG assessment is performed by different midwives), and may serve as a reminder for possibly dangerous patterns, they do not completely eliminate the reasons for manual CTG misinterpretation. Further, their application is quite time-consuming, error-prone and cumbersome, in particular for unexperienced midwives or obstetricians.

There have already been attempts in the prior art to automate the process of CTG scoring. However, none of these systems has proven particularly successful. CTG interpretation systems already available on the market are restricted to the calculation of the fetal heart rate variability, special indices or factory-defined scores. The calculated variability, indices and scores do not match the well-known score tables hitherto used for manual CTG evaluation.

There have also been attempts to implement complete score tables in automatic CTG interpretation systems, but none of them has been successful up to now, and none of them was commercially sold.

The present invention relates to an improvement for automatic CTG interpretation systems. The inventor has found that one major reason for former interpretation systems not having been accepted by the user was that the factory-set evaluation criteria did not correspond to the criteria expected by the user.

It is therefore a major objective of the present invention to provide an apparatus and a method for evaluating the fetal condition prior to or under birth, according to the kind described above, that provides the flexibility of adaptation to each single user's needs.

This objective is solved, in a first embodiment of the invention, in an apparatus of the kind described above, by
rule storing means operatively connected with said rule based operating means;
connection means for connecting said rule storing means with rule editing means;
said rule editing means providing
a rule edit mode for setting up new rules or changing existing rules,
a rule restore mode for restoring information on new or changed rules in said rule storing means;
wherein said rule based operating means is set up to operate according to the information restored in said rule storing means from the time of restoration.

According to the present invention, the apparatus does not calculate according to or generate fixed criteria, nor does it operate according to fixed instructions. Instead, its operation is performed under the control of rules (typically, logic or algebraic rules) stored in a rule memory. Those rules are subject to modification by the user. For this purpose, the rule memory may be connected with rule editing means. (It will be appreciated that this may be a permanent connection or a connection set-up only for editing purposes and cut later. The first alternative is particularly feasible in case the apparatus is connected with a central monitor or station, or if it is equipped with a screen display anyway. The second alternative is particularly useful for stand-alone monitors without screen display).

The rule editing means provides a first operating mode, namely a rule edit mode for setting up new rules or changing existing rules. This mode enables the user either to define his own rules (instead of, or in addition to, any default rules which may already be stored in the system), or simply to modify a predefined rule. There are several advantageous possibilities of modifying existing rules: For example, let us assume that a rule defines the conditions under which a contraction in the TOCO channel is identified. One of these conditions is the minimum amplitude of the TOCO trace over the TOCO baseline (this baseline being called "resting tone"). In case the user feels that his fetal monitor is too sensitive to contractions, i.e. designates patterns as contractions which the user would not regard as such, he may increase the minimum amplitude. In general, rule editing comprises addition of, deletion of or modification of rules.

Another feasible approach of rule modification is simply to request the system to switch to another predefined rule. In this case which will be discussed in more detail below, the user even does not have to alter the rule itself. The term "changing existing rules" as used herein covers both of the above cases.

In a second operating mode called "rule restore mode", the rule editing means restores the new or changed rules in the rule memory (i.e. stores the new rule, or replaces the existing rule by the changed rule). In case the user has simply switched to another predefined rule or set of rules, it is sufficient to restore an identifier marking the selected predefined rule. Both cases, namely restoring of rules or of identifiers, are covered by the wording "information on rules" as used herein. In order to restore a rule or information on a rule, it will be advantageous to use an erasable memory such as an electrically erasable memory which keeps its contents even if disconnected from the supply voltage. Such memories may e.g. be semiconductor memories such as a battery-buffered RAM (random access memory) or a Flash EPROM (electrically programmable read-only memory). However, there are other storage media which do not require to be erased before new information is stored, such as magnetic media (disks, tapes) or optical disks.

The apparatus is set up such that the restored information is subsequently used, instead of the preceding information. That is, upon restoration of rules or information on rules, the apparatus will use the revised rules to assess the CTG and thus the fetal condition.

A "rule" may be any logic or associative instruction controlling operation of the fetal monitor, a connected central station or any other device in which the present invention may be incorporated. Examples of "rules" will be given in the detailed description. Preferably, a "rule" is defined just in the way the user (expert) would write down an algebraic expression, e.g.

"if A<rel>B then C"

wherein <rel> stands for a mathematical (<,>,=,#
etc.) or a logic (AND, OR, NOT, EXOR etc.) relation.
A more general expression for a "rule" is "if <condition> then <statement>"

wherein <condition> can be any mathematical (algebraic, logic etc.) condition; it can even be a combination of subconditions interconnected by logical operators, or the like.

Such a "high-level" rule may be translated into the "language" (machine instructions) of a processor, such as a microprocessor or other CPU (Central Processing Unit), by a compiler; or it may be interpreted—either directly or in a transformed form—by an interpreter, preferably implemented in a language like PROLOG or LISP. When the underlying task is not extremely time-critical, the preferred way is to use a rule interpreter such as PROLOG. However, it will be appreciated that a compiler may be used as well. Further, may be other ways of defining the operating rules of the fetal monitor, such as editing assembly language instructions or the like (although this way is not very comfortable).

In the apparatus according to the present invention, the fetal heart rate and maternal labour may be detected by any convenient technique, e.g. one of the above described techniques. Therefore, the "first detection means" and the "second detection means" recited in the first paragraph of this description may be appropriate detectors receiving the signals of a fetal heart rate or a TOCO transducer. For example, the fetal heart rate transducer may be a prior art ultrasound transducer, in which case the first detection means comprises a demodulator for detecting the Doppler shift in the ultrasound signal; preferably, it also includes an autocorrelator for reliable detection of the fetal heart rate. The details of these detectors are prior art and will therefore not be described or claimed in detail here.

The processing means recited in the first paragraph of this description produce quantities of possible diagnostic information. Such quantities may e.g. be the duration or the amplitude of events (such as decelerations or contractions) in the time traces of the fetal heart rate or maternal labour, the begin or end, or the first derivative, of such events, areas, but also variability, statistical data like mean, standard deviation, center in a direction, center of mass of a curve etc. In general, a quantity as used herein is any feature or property derived from the original time traces of FHR or TOCO and of possible use for the interpretation and assessment of the CTG. A "derived parameter" is e.g. a (possibly weighted) combination of such quantities, or a parameter otherwise derived from a quantity (like the first or second derivative, a maximum etc. of a quantity).

The present invention enables the user (the expert) to modify the operating rules of the fetal monitor and/or an associated central station in a very easy way, preferably in interactive mode. It has turned out that it is hardly possible to adapt fixed operating rules such that they meet every single user's needs. This is partially due to local differences; it also depends on the experiences of a physician or a hospital and on their specific requirements. Therefore, even a system with fixed rules fulfilling the requirements of a single user would not fulfill the needs of another user. The present invention overcomes this disadvantage by providing flexibility, so that every user may adapt the fetal monitor or like apparatus to his specific needs. In particular, the user may either make an overall adaptation only—e.g. by selection of one of the known score tables—, or he may adapt the fetal monitor very specifically, e.g. by altering one of the score tables, by setting up a new score table, or by adapting other parameters (he may e.g. redefine what a "contraction" is, i.e. set his own criteria for detection or validation of a contraction).

Preferably, the apparatus according to the present invention contains at least one predefined set of rules. In the case of a score table, this could be one of the famous known score tables like the "Hammacher" score table. Predefinition of such a score table, or other parameters, has the advantage that modification becomes easier—the expert will usually have to adapt an existing set of rules only (which may require a few changes only), instead of defining a complete set of rules. Advantageously, the apparatus provides even several "default" sets of rules. In case of the score tables, these could e.g. be some of the score tables known in the art, like the "Hammacher" score table, the "Fischer" score table etc. Selection among several score tables makes adaptation even easier, as the score table closest to the expert's expectations may be selected as the basis of the editing process.

The ability of the system to manage several score tables—e.g. some predefined "default" score tables, and some user-defined score tables—has further related advantages. For example, let us assume a fetal monitor or a central station handles four predefined score tables and three user-defined score tables. Different ones of these score tables may then be selected, even in the same hospital or the same delivery room, from patient to patient (provided their status requires a different kind of monitoring; typical examples where a score table different from the "standard" score table could be required are e.g. high-risk delivery or expected twins). In case two physicians have different personal preferences, each of them could even select his preferred score table, although both use the same fetal monitor. Needless to say that the above remarks apply not only to the score tables, but also to other operating rules of the fetal monitor or the central station.

Another advantageous approach is to "configure" the fetal monitors in a hospital in uniform manner. Such could e.g. be performed by connecting all of the fetal monitors to a common central station, and having fetal assessment done there for all fetal monitors. This requires adaptation of the central station only. However, even if only stand-alone fetal monitors were used, there is an easy way of solving the underlying problem, namely to edit the rules of one fetal monitor only, and then to transmit the revised operating rules directly from the reconfigured fetal monitor to other fetal monitors (of course, appropriate interfacing circuitry is required). In this way, it is possible to avoid the reconfiguration of all fetal monitors in the hospital (which would be a quite time-consuming process).

As will be apparent from the foregoing, it is a major aspect of the present invention to provide fetal condition assessment means including adaptable and/or user-configurable score tables. The score table, on the other hand, serves as an "alarm table" as well, as a high sum-score, or a sum-score exceeding certain limits, indicates a clinically dangerous situation. However, it will be outlined below that other configurable operating rules, like validating or classification rules, are advantageous as well.

In a preferred embodiment of the present invention, the rule editing means provides a retrieve mode for retrieving rules or information on rules from said rule storing means. This feature is helpful if it is intended to modify a rule, or information (e.g. selection) on a rule, instead of defining new rules (where no retrieval of existing rules or information on rules is necessary). Of course, one could practice the present invention by offering a "new rule edit" mode only, but the possibility to retrieve existing information makes handling considerably easier. In case a retrieve mode is provided, it is further advantageous if the rule editing means provides a modify mode for modifying the retrieved rules, wherein, in the restore mode, the modified rules are stored in the rule storing means.

In another preferred embodiment, the rule editing means provides a definition mode for defining new rules, wherein, in the restore mode, the modified rules are stored in the rule storing means. This is the mode for definition of completely new rules (it will be appreciated that the present invention would also work, however with less comfort, if only modification of existing rules were possible).

It is of advantage if the rule editing means provides a select mode, wherein rules stored in the rule storing means are offered for selection, and information on the selected rule or rules are stored in the rule storing means. This is a mode of operation in which the inventive apparatus already contains some predefined, or user-edited, rules. The select mode allows to choose (to "activate") one, or a set, of these rules. It will be understood that the rules themselves need not be edited in this case; therefore, it is sufficient to store the information which of the existing rules is to be activated.

The rule editing means includes, in another advantageous embodiment of the present invention,
display or recording means, preferably a personal computer, a CRT display or a printer, and
edit control means, preferably an expert interface.

Use of a computer, in particular a personal computer (PC), has the advantage that the edit control means (typically, a processor or a CPU under control of an appropriate control program) may also be installed on the PC, i.e. the expert interface would run on the personal computer, such that the fetal monitor need not contain all the associated hardware and software (which would, in turn, reduce the fetal monitor's manufacturing cost and thus its price). However, a CRT, LCD, plasma etc. display may be used as well, if the appropriate control functions are incorporated in the fetal monitor. It is even possible to use a printer, plotter or other recording means for communication with the expert. One could e.g. regard to use the internal printer of a fetal monitor for human interface purposes in case a PC or display is not available. Another possibility for communication with the expert is to use a flat LCD display with handwriting detection (such displays are already commercially available).

As already described above, the score tables are a major aspect of the present invention. Therefore, the inventive apparatus is preferably characterized in that the rule based operating means includes fetal condition assessment means for calculation of a score according to rules stored in the rule storing means in dependence of the quantities generated by the processing means, or parameters derived thereof, or of the fetal heart rate trace or of the TOCO trace. Further, the fetal condition assessment means may preferably assign single scores to events observed in said quantities or derived parameters, or the fetal heart rate trace or the TOCO trace, according to rules stored in the rule storing means, and a sum-score of all single scores may be calculated. The "sum-score" thus represents the overall fetal assessment (it may be obtained by simple addition of the single scores, but this is not a necessary condition; other examples of calculation of the sum-score are weighted addition, multiplication etc.). A high sum-score indicates fetal distress. Thus, the sum-score is also some kind of alarm indicator. In another advantageous embodiment of the present invention, the fetal condition assessment means therefore operates in combination with an alarm handler, said alarm handler generating an alert or an alarm if the sum-score exceeds a predefined limit. Alarm output may be performed in any convenient manner, e.g. optical alarm (flash red lamp), acoustic alarm, send alarm message to central station etc. As the sum-score is quite sensitive, it is also possible to generate different levels of alarm, depending on the sum-score (e.g., an optical alarm (various colours, sizes, symbols etc.) if the sum-score indicates a prepathologic assessment and, additionally, an acoustic alarm if the sum-score is pathologic). In general, the alarm is generated if various patterns are pathologic. It is necessary to mention that there are also sum-scores wherein a low sum-score indicates fetal distress, and that the alarm condition may be influenced by other critical parameters (which are not necessarily represented by a high or low sum-score) as well. Therefore, the above explanations relate to a typical and advantageous embodiment of the present invention, but do not limit its scope.

In a useful environment, the rule storing means contains at least one set of predefined rules for assigning scores to events. This is a "predefined" score table which may be either one of the common score tables like the "Hammacher" score table, or another factory-defined score table. Likewise, in the select mode, a selection may be provided among at least two of sets of predefined rules, wherein the information stored in the rule storing means is information on the selected set of predefined rules. Again, it is understood that the preceding remarks apply not only to rules constituting a score table, but to other rules, such as validating or classifying rules (see below), as well.

One problem encountered with automatic CTG scoring, as compared to manual scoring, is that, upon occurrence of an alarm (or, in general, a high or low sum-score), the reason for the alarm may not be evident. In other words, several parameters may have contributed to a high sum-score, but there may be no indication which these were. It is also possible that the high sum-score results from a single parameter only (which contributed a very high or very low score).

It is important for a correct diagnosis to know the reasons for an alarm, as the necessary therapeutic measures may depend on the parameter(s) causing the high (or low) sum-score and, thus, the alarm. This is no problem in the case of manual scoring, as the parameters, and their scores, are listed on a sheet of paper (usually, the midwife prepares the score which is then assessed by the obstetrician). On the other hand, if the CTG is automatically scored as in the present invention, the scores are not listed specifically. Of course, it would be possible to generate an automatic printout, or a screen window, in case of an alarm. However, in case an internal printer of the fetal monitor is used, printout requires a considerable amount of time (during which the time traces of FHR and TOCO cannot be recorded, or at least not with the same resolution as usual). Further, subsequent short-intervallic alarms would cause the printer to print scores continuously—it would not be possible to record any further time traces at all! One could solve this problem by providing two printers or other technical measures, but all of these would be complicated and costly. Similar considerations apply to a display in a central station. As soon as a "window" providing scoring information is opened on the screen, it covers the FHR and/or TOCO time traces (which are of importance for the diagnostic assessment as well) at least partially.

Therefore, automatic retrieval of scoring information is no feasible solution. The present invention provides a solution to the underlying problem by means of an apparatus for evaluating the fetal condition prior to or under birth, wherein rule based operating means include reasoning means, in particular a reasoning processor, retrieving reasoning information related to a sum-score upon user request. That is, according to one inventive aspect, the alarm itself does not cause retrieval of information related to the sum-score. However, in case the clinical staff decides that further information on the reasons of the alarm are necessary to assess the fetal condition reliably, a request may be made, in which case the fetal monitor or the central station would retrieve the required information. This process ensures that information is only retrieved in case there is a real necessity therefor, i.e. false or unimportant alarms will not cause the FHR or TOCO recordings to be covered by score information. On the other hand, if a clinical person decides to check the score, he or she will have the opportunity to check the recordings before they are covered by a window (on a screen) or before they are interrupted (on a printer or recorder).

The user request may be communicated to the inventive apparatus in any convenient manner, e.g. by pressing a special "reasoning" key or a keystroke sequence on the fetal monitor or a central station, by request via a computer mouse or a keyboard, a touchscreen etc. The reasoning processor may be either a separate microprocessor or a program module of a microprocessor or CPU used for other purposes as well.

The term "information related to a sum-score" does not necessarily mean that a complete score table is retrieved from a memory such as a rule storing memory. Instead, it may also be information on which the sum-score is based (i.e. information preceding the scoring process) or information derived from a certain score. Typical and advantageous information retrieved by the reasoning processor upon user request may be:
  the sum-score itself,
  a clinical assessment derived from the sum-score (e.g., "normal", "prepathologic" or "pathologic"),
  the single scores assigned to events,
  the quantities or derived parameters, or the fetal heart rate trace or the TOCO trace, leading to said events, or their values, or the time of their occurrence,
  explanations on the reason of the alarm (like bradycardia, loss of signal, etc.),
  further hints on the fetal situation (like the duration of an event).

Preferably, the information to be retrieved upon user request is also subject to expert (rule) editing, i.e. the expert may e.g. specify whether he wants the scores assigned to single events, or their clinical assessment, or other information to be retrieved in case a user request occurs.

The apparatus according to the present invention may reproduce score information whenever a user request occurred, i.e. even in the absence of an alert or alarm. That is, an obstetrician or midwife may gather information on the fetal condition at any point in time. However, in order not to confuse clinical personnel, a preferred embodiment of the invention is characterized in that the reasoning means is only active after the occurrence of an alert or alarm.

In another advantageous embodiment, the reasoning means includes several operating levels, in particular accessible by subsequent user keystrokes, each operating level retrieving different reasoning information. That is, depending on the nature of the user request, different reasoning information may be reproduced. In particular, sequentially accessible operating levels may be provided, wherein the reasoning information becomes more detailed from level to level. The obstetrician or midwife may thus retrieve information until a level providing a satisfying diagnosis is reached, thus avoiding retrieval and reproduction of unneccessary information. For example, in a first level, the clinical assessment ("normal", "prepathologic", "pathologic") of the CTG may be reproduced, preferably by display or printout of the retrieved information. In a second step, i.e. if the user request is repeated, the sum-score (plus the score table on which said sum-score is based) may be retrieved. A third step (=further user request) retrieves the alarming parameters, i.e. the parameters contributing to the sum-score; a fourth step retrieves their actual values, and a fifth step the times when the related conditions occurred in the FHR or TOCO time trace.

The above example is based on the assumption that repeated user requests (e.g. subsequent depression of a "reasoning" key) retrieve and reproduce stepwise more and more detailed information. In an alternate embodiment, there could also be direct access to a certain "reasoning" level, e.g. by specifying the number of the level over a keyboard. A third alternative provides a multiplicity of "reasoning" keys, e.g. labeled "Assessment", "Sum Score", "Parameters", "Values" etc. for direct access to a reasoning level. The reasoning levels, their order and the information retrieved in each level may also be subject to expert editing.

It is understood that the above considerations on the "reasoning" process and the related apparatus apply not only to a fetal monitor or a central station providing expert rule editing. Instead, the reasoning means may also be used in a "standard" fetal monitor or central station, i.e. without the feature of expert editing.

Another aspect of the present invention relates to preprocessing of the fetal heart rate trace and the TOCO trace. The purpose of preprocessing is to extract quantities describing the FHR and TOCO time traces such as decelerations, contractions, amplitudes, statistical data, as well as variability etc. (see above). The present invention provides, in an advantageous embodiment, processing means which comprise time domain preprocessing means for preprocessing the fetal heart rate trace in the time domain. Specifically, the following steps are performed in the time domain:
  a) removal of jumps in case a positive or negative jump exceeds a predefined limit. As vertical jumps in the time domain disturb the spectrum by overlaying an si-function (wherein the weight of the si-function is proportional to the height of the jump), such jumps are removed in case they exceed a predefined, preferably adjustable limit (a limit is necessary to identify a jump as such; i.e. sudden FHR changes should not be removed!);

b) removal of DC components from the fetal heart rate trace, in order to simplify further processing, c) appliance of a spectral leakage-reducing window, in particular a Hamming window. As the limited duration of a time domain data block subject to Fast Fourier Transformation (see below) results in spectral leakage, a window function is already applied, in preparation of the subsequent transformation into the frequency domain.

According to the present invention, further processing is then performed in the frequency domain. For this purpose, preprocessing means are provided which include frequency transformation means, in particular Fast Fourier Transformation means, for transforming a fetal heart rate trace into the frequency domain. Despite the hard- and/or software required to perform frequency transformation, it has been found useful—in contrast to prior art approaches—to investigate the FHR trace also in the frequency domain, in order to obtain parameters reliably and completely describing the fetal heart rate. The Fast Fourier Transformation (particularly, a Fast Hartley Transformation) may be performed by a special FFT processor, or by an appropriate program controlling a microprocessor or other CPU which is also used for other purposes. In practice, the latter solution has been found satisfying, as the spectrum has to be calculated every 30 to 60 seconds only ("scoring" is even performed in longer time intervals, e.g. 10 minutes, wherein the last 30 minutes are the basis for the assessment).

In preparation of the assessment of the calculated spectrum (the FFT may produce an absolute spectrum and a power spectrum), a filter function is preferably applied to it, in particular a linear or an exponential filter function with expert-definable characteristics. The purpose of this filter is primarily to reduce the amplitude of the low-frequency components.

According to a further preferred and most important feature, the variability of the fetal heart rate is derived from the spectrum. The inventor has found that the precision of FHR variability calculation may be considerably increased if performed in the frequency domain. Therefore, fetal heart rate (FHR) variability detection means are provided including frequency detection means, said frequency detection means calculating the frequency of FHR variability by identification of the spectral line with the highest amplitude in the associated spectrum, preferably in a predefined region of said spectrum. That is, the maximum spectral line indicates reliably the frequency of FHR variability. This is particularly true if the above-mentioned filter suppressing low-frequency components has been applied, so that no low-frequency spectral lines may erroneously be identified as the frequency of variability. In order to increase accuracy further, it is possible to search only a limited region of the spectrum for the spectral line of maximum amplitude. This may e.g. be a predefined window in which variability is usually found. In a more sophisticated environment, the limits (and/or the width) of the spectral window are adaptive, i.e. once the true frequency of variability has been found, the window is automatically adjusted to the expected region. The limits, or the width, of the window may also be subject to expert editing. In general, the formula for identification of the frequency of variability is $$f_{VAR} = \max (F(i\Delta\omega))|_{i=m}^{M}$$

wherein $F(i\Delta\omega)$ denotes the single spectral lines, i is an index running over a predefined spectral range (and possibly subject to adaptation and/or expert editing), and $f_{VAR}$ is the frequency of the fetal heart rate variability.

In similar manner, the amplitude of FHR variability may be detected, namely in that the fetal heart rate (FHR) variability detection means includes amplitude detection means, said amplitude detection means calculating the amplitude of variability as the amplitude of the spectral line of the highest amplitude in the associated spectrum, preferably in a predefined region of said spectrum, plus the amplitude of secondary spectral lines adjoining said spectral line of highest amplitude, provided said secondary spectral lines exceed or fall below predefined limits.

The general formula for detection of the amplitude of FHR variability is $$A_{VAR} = C * \sum_{i=m}^{M} |F(i\Delta\omega)|$$

wherein $F(i\Delta\omega)$ denotes the single spectral lines, i is an index running over a predefined spectral range including the spectral line of maximum amplitude, C is a constant and $A_{VAR}$ is the amplitude of the fetal heart rate variability: That is, not only the spectral line of maximum amplitude is taken as the amplitude of FHR variability, but some "sidelobes" are taken into account as well. This is due to the fact that the variability may be subject to some "jitter" during the period (the "time window") under investigation. Several criteria for selection of the sidelobes may be used, e.g. a predefined number of sidelobes, sidelobes which are not smaller in amplitude than 80% of the main lobe, etc. Like in the case of frequency of variability determination, the criteria and limits of the window for sidelobes may be subject to automatic adaptation or to expert editing.

It will be appreciated that the rules of time and frequency domain preprocessing may, in general, be subject to expert editing as well, i.e. the preprocessing means may operate according to predefined rules stored in the rule storing means and may be subject to editing by the rule editing means. However, only few rules of the preprocessor are of general interest to an expert, such as the duration of the time window for baseline processing and frequency transformation.

It will be evident from the foregoing that the concept of frequency domain investigation of the fetal heart rate, and of variability determination, does not depend on expert control. That is, it may also be applied to a "standard" fetal monitor or a central station without rule editor.

It has already been outlined below that a major aspect of the present invention is full expert control over the rules of the score processor, i.e. the way the score table is built. However, there are further important aspects relating to signal processing between preprocessing and scoring.

The preprocessor performs some basic algorithms on the FHR and TOCO time traces. A second processor, called "trace processor" hereinafter, performs a first detection of events such as decelerations or contractions (the detection of FHR variability may either be incorporated in the preprocessor or the trace processor; this is a matter of choice). The operating rules of the trace processor are also subject to expert control. Therefore, in an advantageous embodiment of the present invention, the rule based operating means includes trace processing means for calculation of parameters from the fetal heart rate trace and/or from the TOCO trace or from the related spectra, and/or for identifying candidates for events, in particular for accelerations, decelerations or contractions.

The trace processor thus identifies possible candidates for events. In order not to miss a possible event, it is preferably not very specific. Therefore, validation is necessary. In a further advantageous embodiment of the present invention, the rule based operating means includes therefore validating means for validating possible candidates for events according to rules stored in the rule storing means. By editing those rules, the expert has full control over the validation process and thus over the events taken into account and processed.

Validated events may now be classified. According to an advantageous embodiment of the present invention, the rule based operating means includes classification means for classifying validated candidates for events according to rules stored in the rule storing means. These rules are of particular importance for the subsequent scoring process; they will be discussed, as well as their editing process, in the detailed description. They may e.g. be used to classify a validated deceleration as a "late deceleration" (with respect to a contraction), which is an important clinical event.

Further useful processors include statistics generating means, in particular a statistics processor, for generation, storing and retrieval of clinically relevant statistical data, and trend generating means, in particular a trend buffer, for generation, storing and retrieval of clinically relevant time compressed trends.

All of the above processors may either be separate microprocessors or other CPU's, or control programs for a multiple-use processor. Like in the case of the score processor, they may include a factory-set of default rules, such that expert editing becomes easier.

The present invention further relates to a method for evaluating the fetal condition prior to or under birth comprising the steps of:
 detecting the fetal heart rate,
 detecting maternal labour,
 generating quantities derived from the fetal heart rate and/or the maternal labour representative of possible diagnostic information,
 extracting, validating, classifying or scoring said quantities, or derived parameters, according to predefined rules stored in a rule memory,
wherein said method is characterized by the steps of
 connecting the rule memory with rule editing means,
 setting up new rules, changing existing rules or selecting predefined rules or a set thereof,
 storing said new or edited rules or information on the selected rules or set of rules in said rule memory.

Further important aspects of the present invention will be found in the claims and the detailed description.

Figure 2:
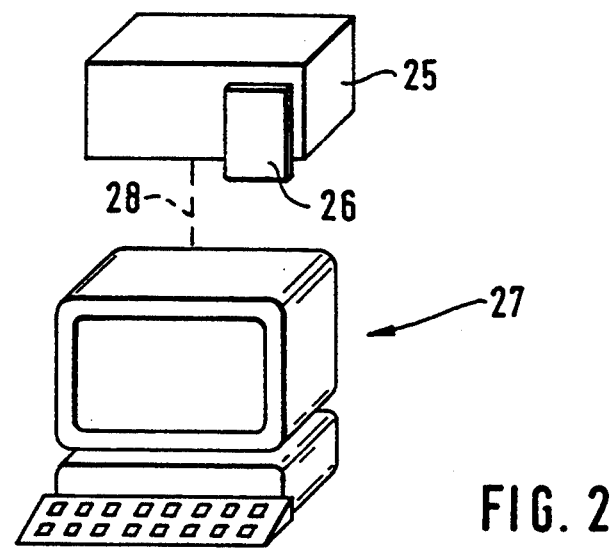
Figure 3:
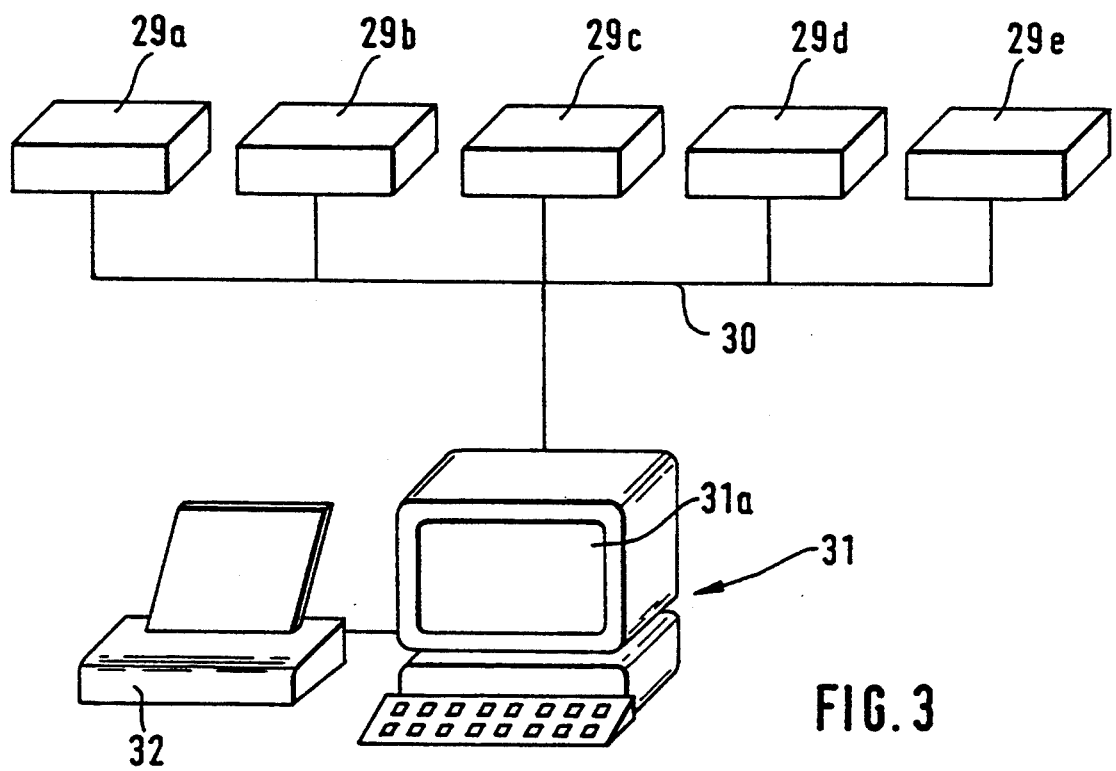
Figure 4:
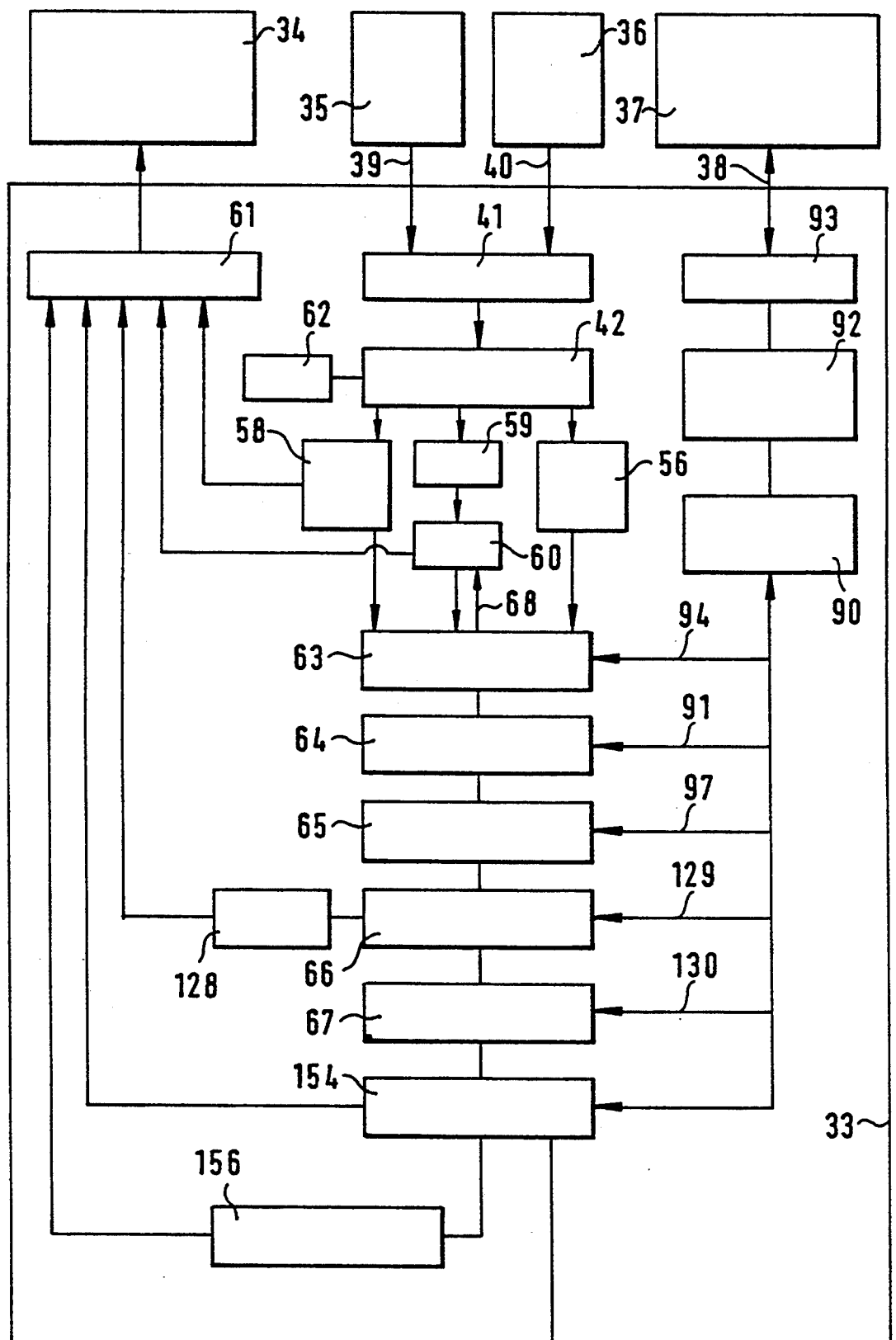
Figure 5:
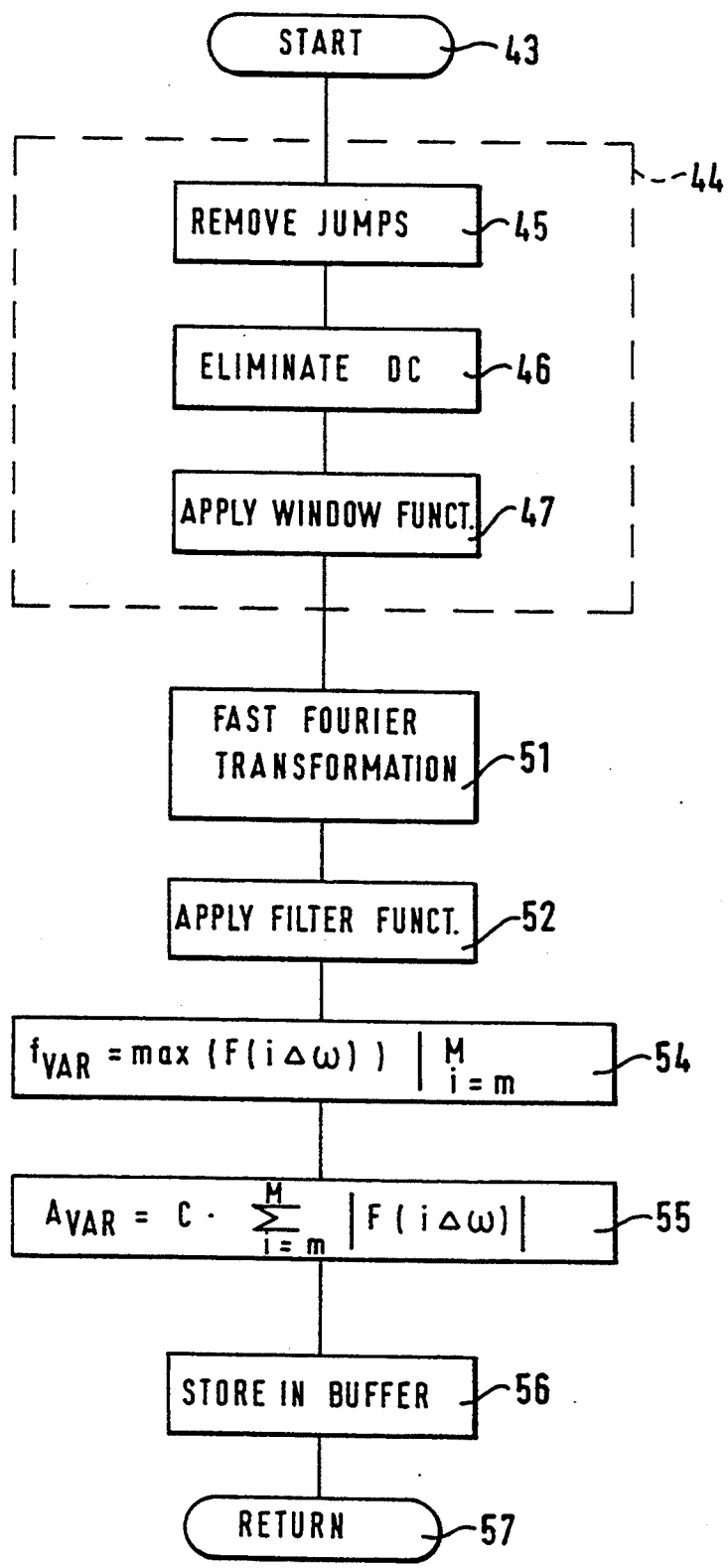
Figure 16:
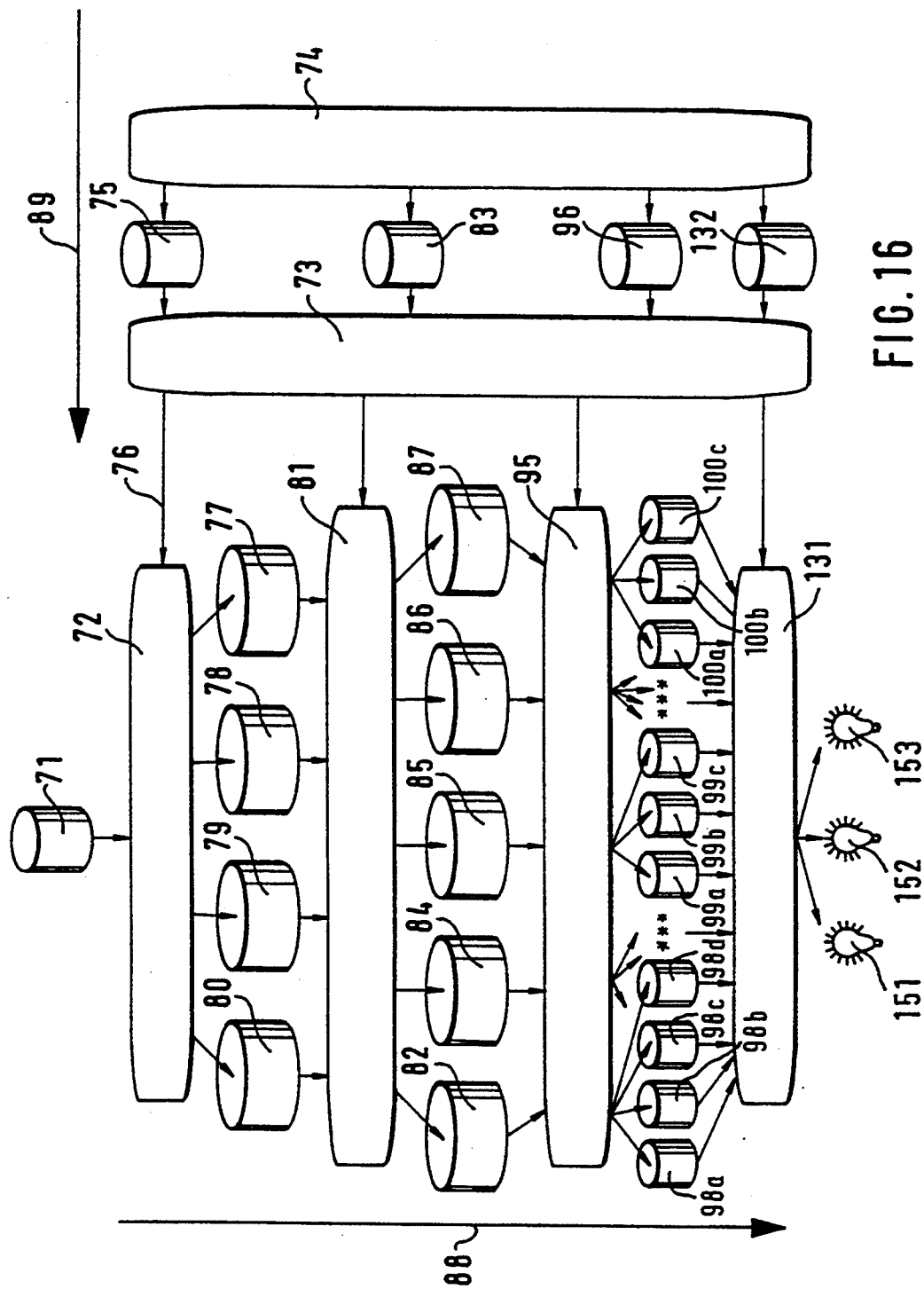
Figure 17A:
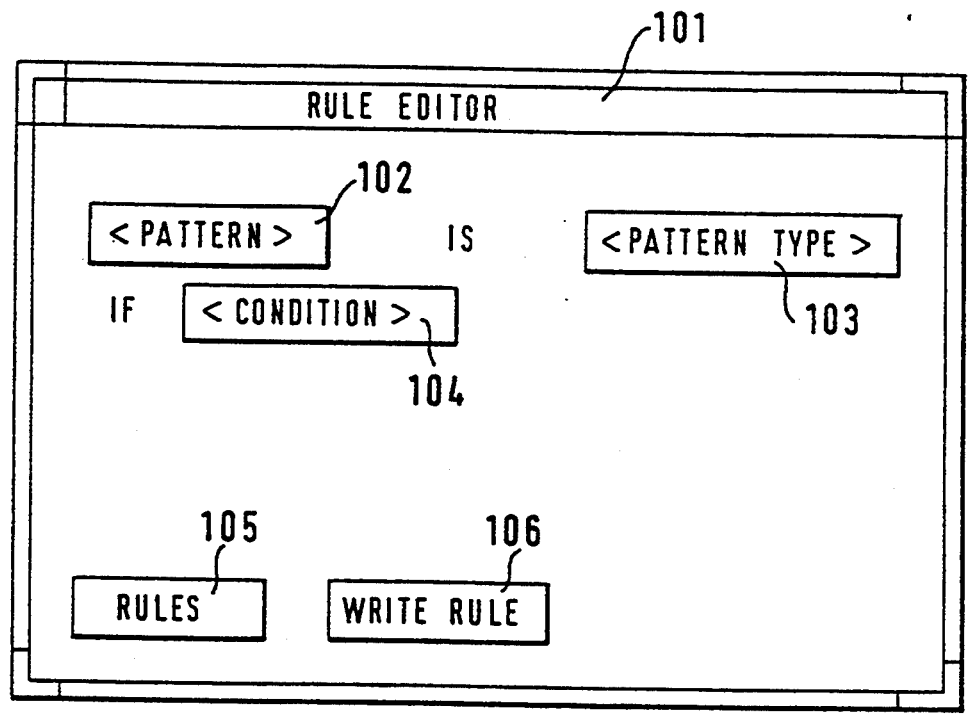
Figure 17B:
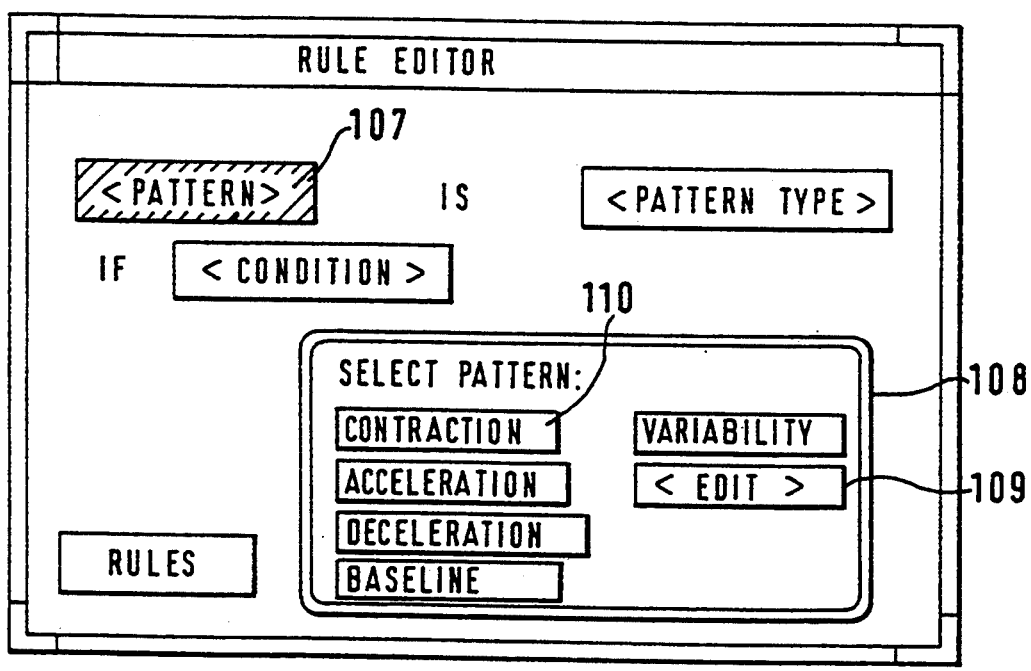
Figure 17C:
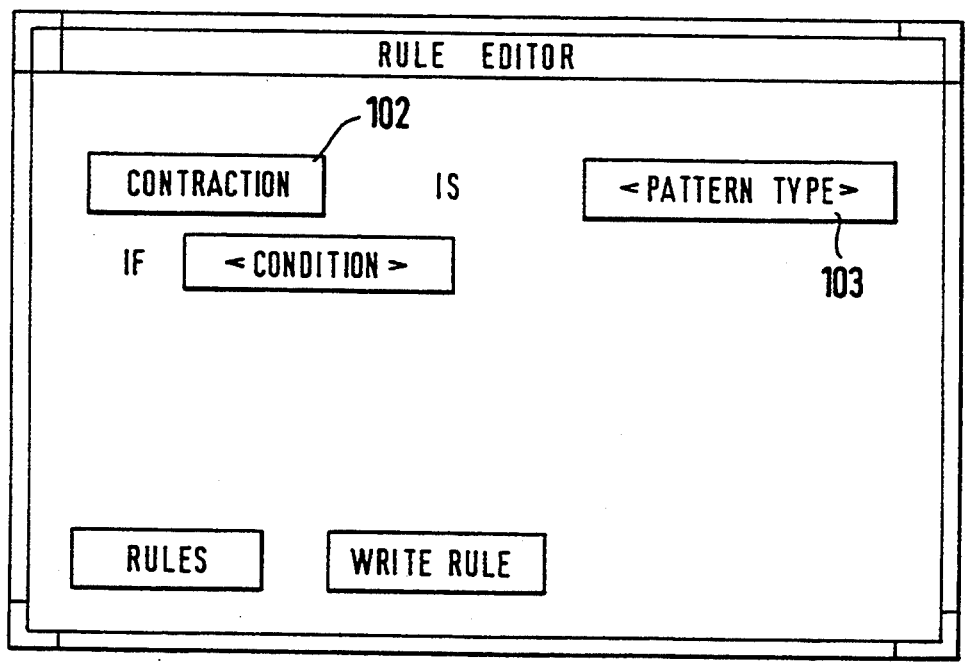
Figure 17D:
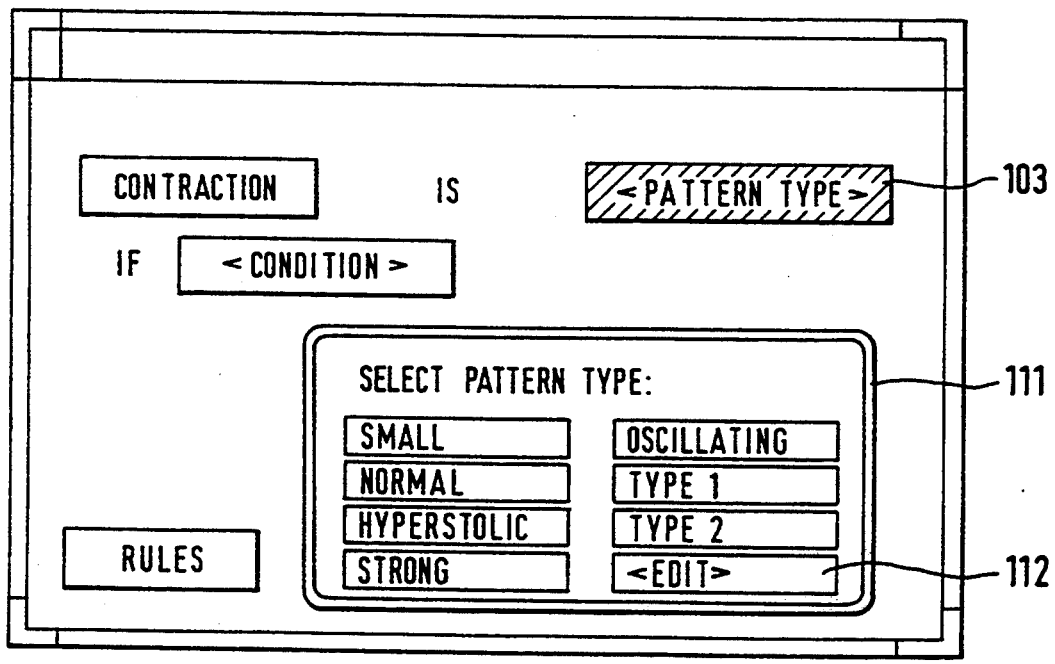
Figure 17E:
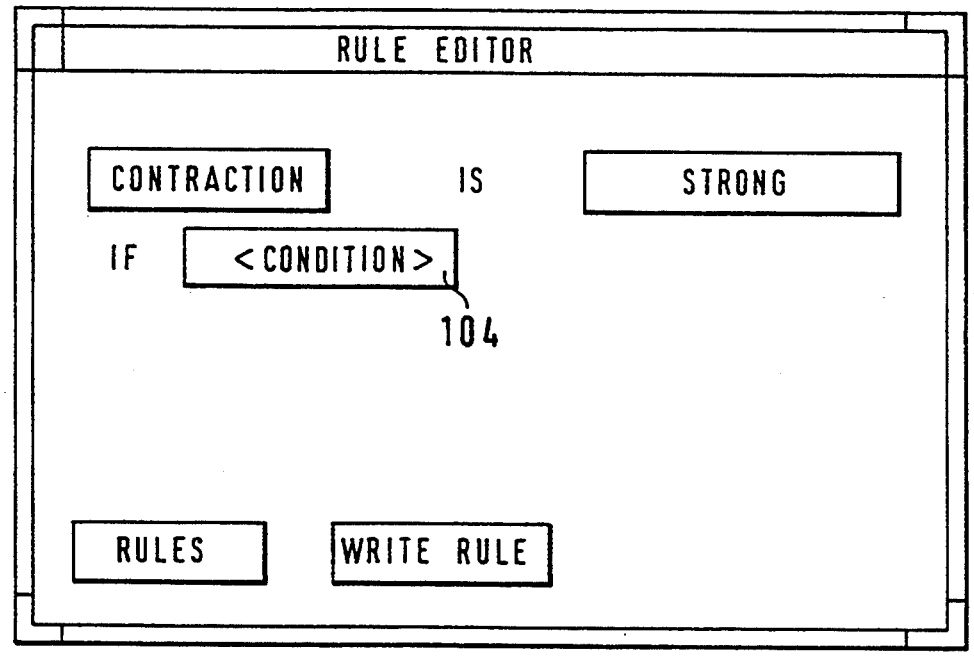
Figure 17F:
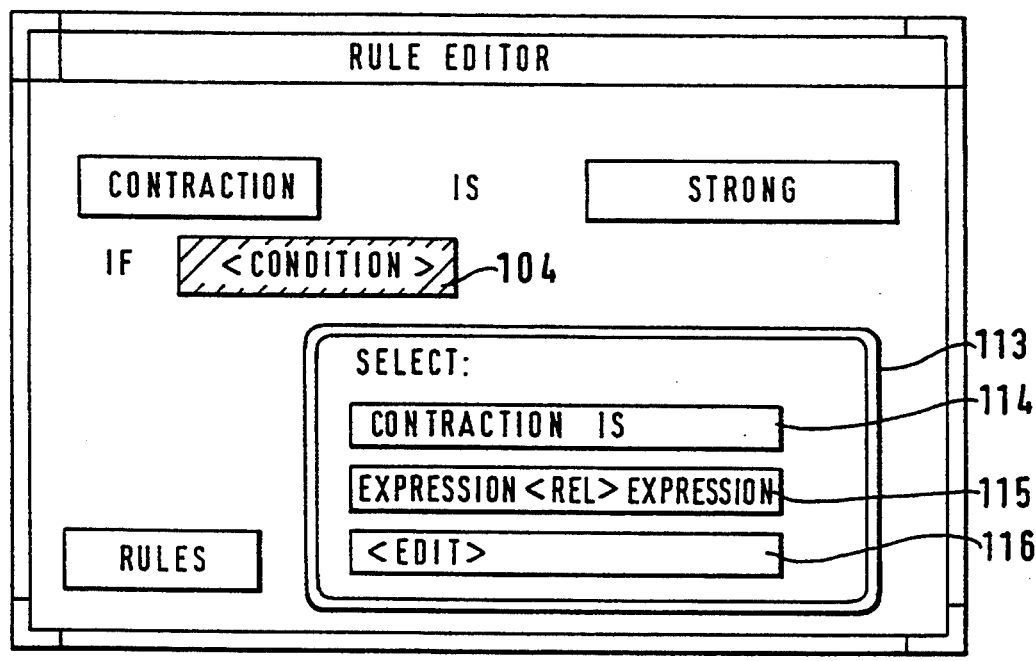
Figure 17G:
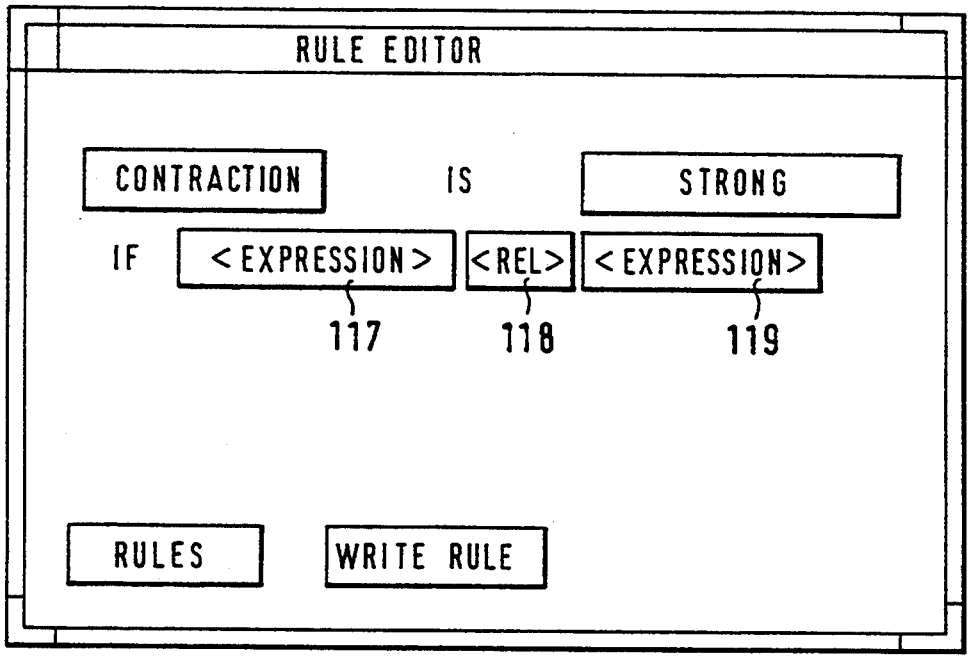
Figure 17H:
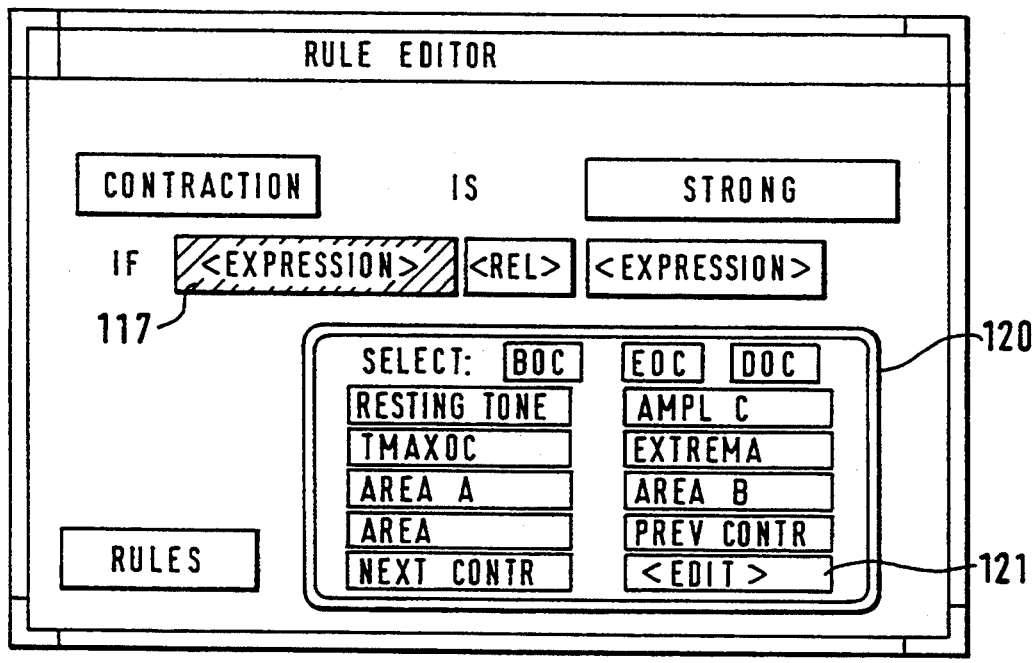
Figure 17I:
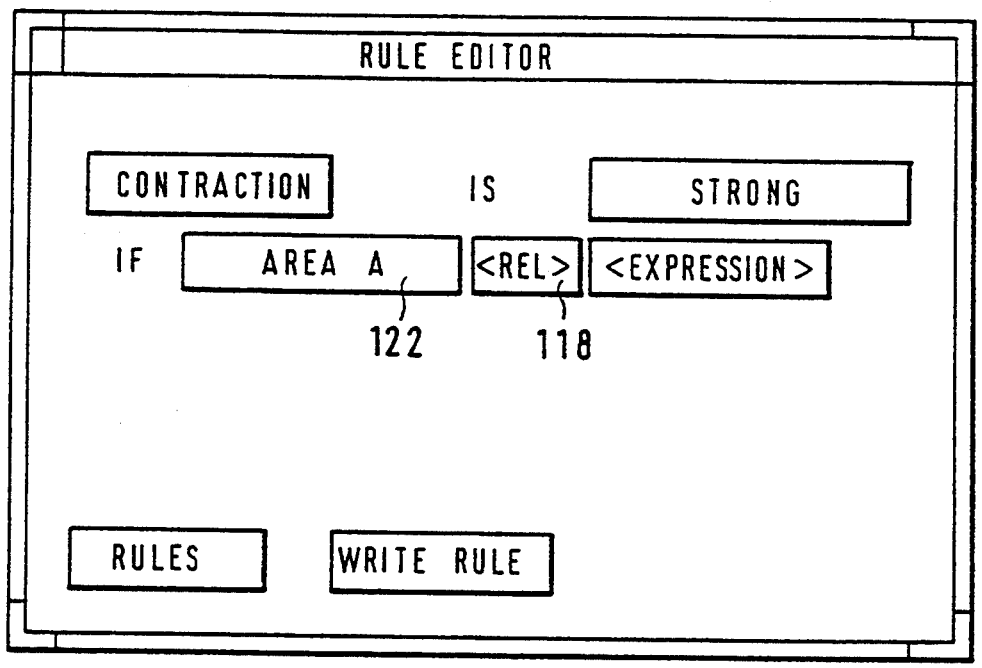
Figure 17J:
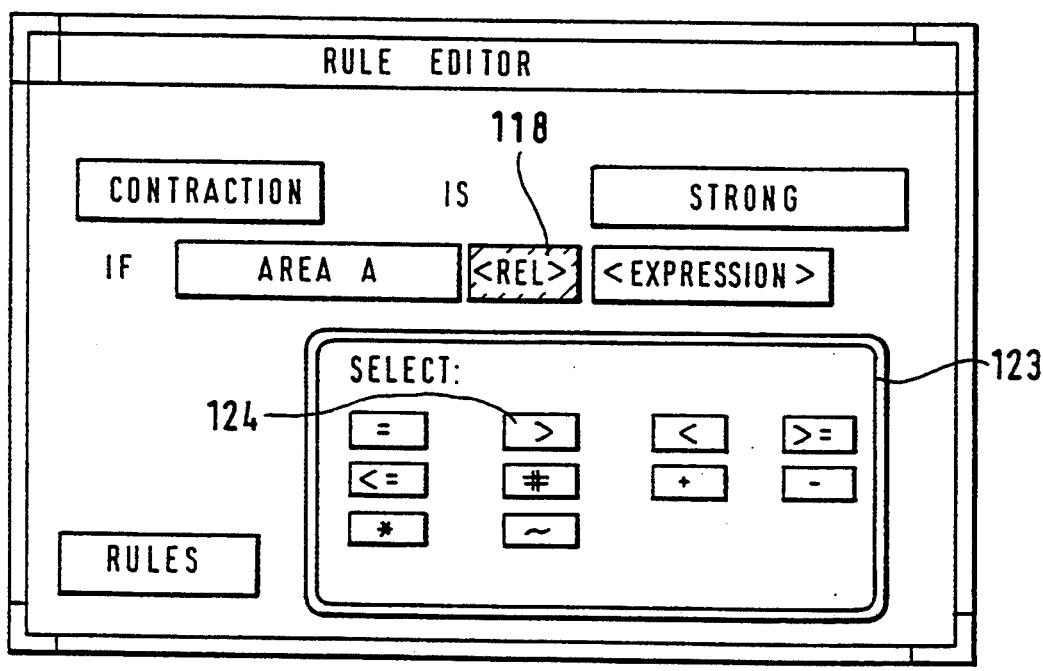
Figure 17K:
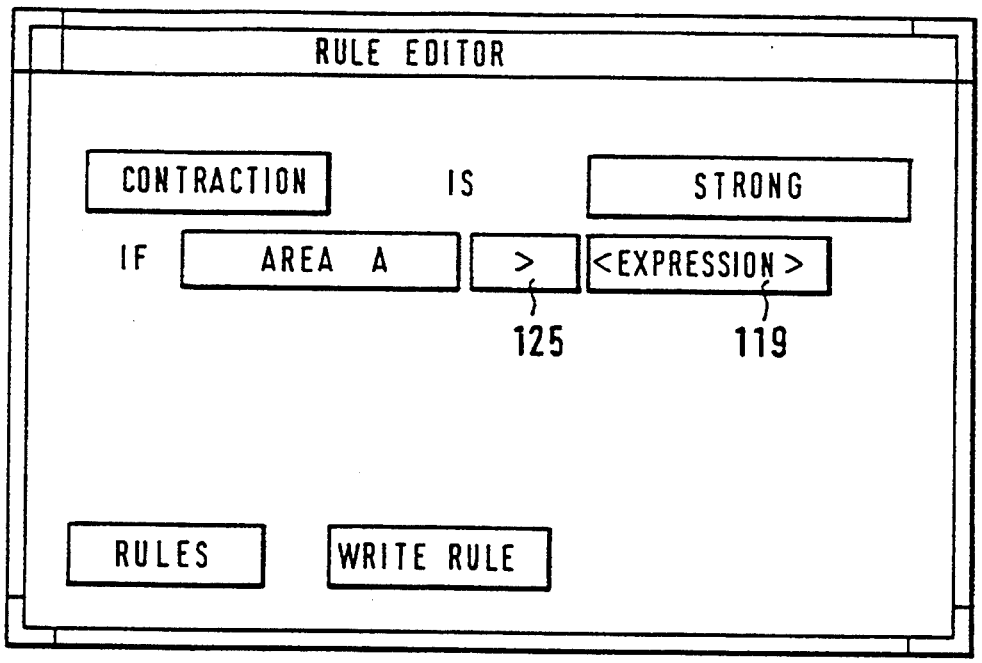
Figure 17L:
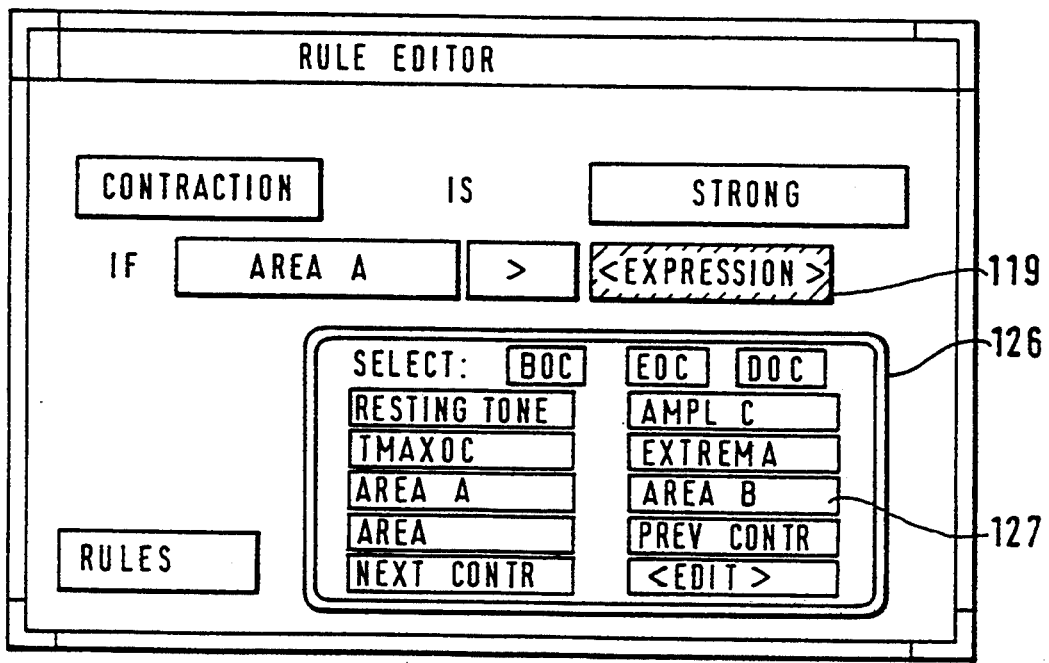
Figure 17M:
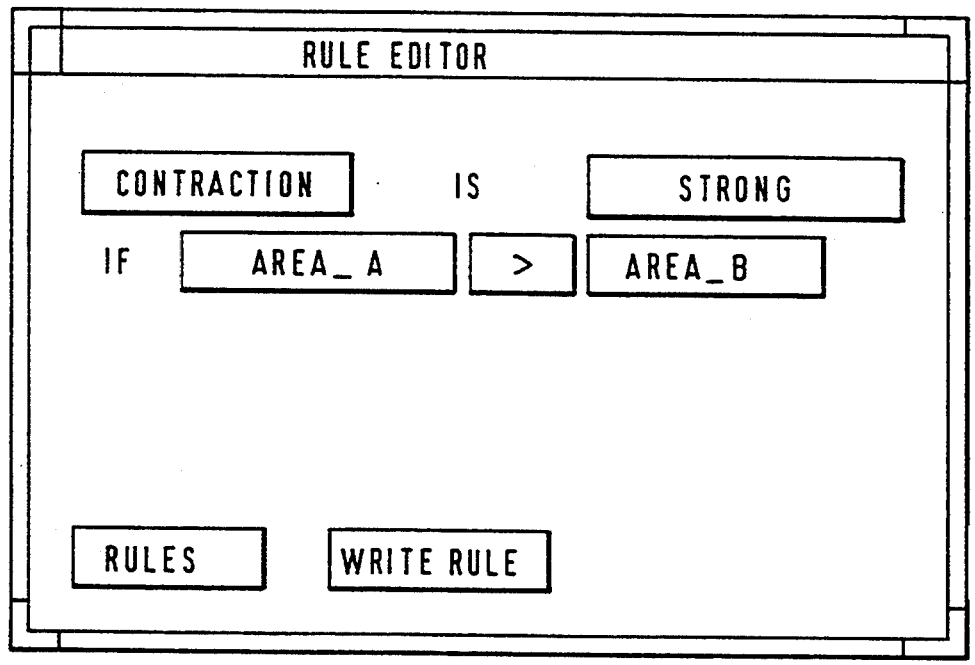
Figure 17N:
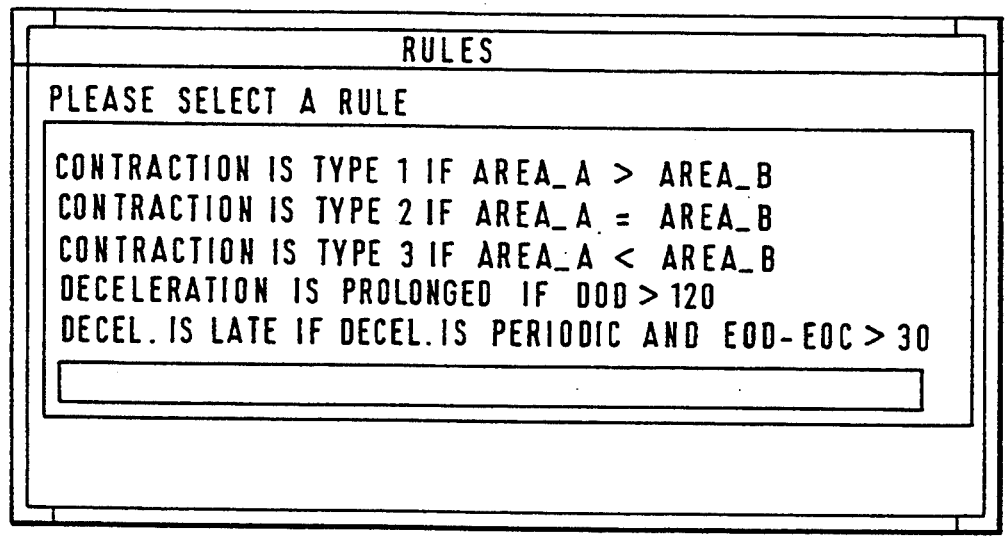
Figure 18:
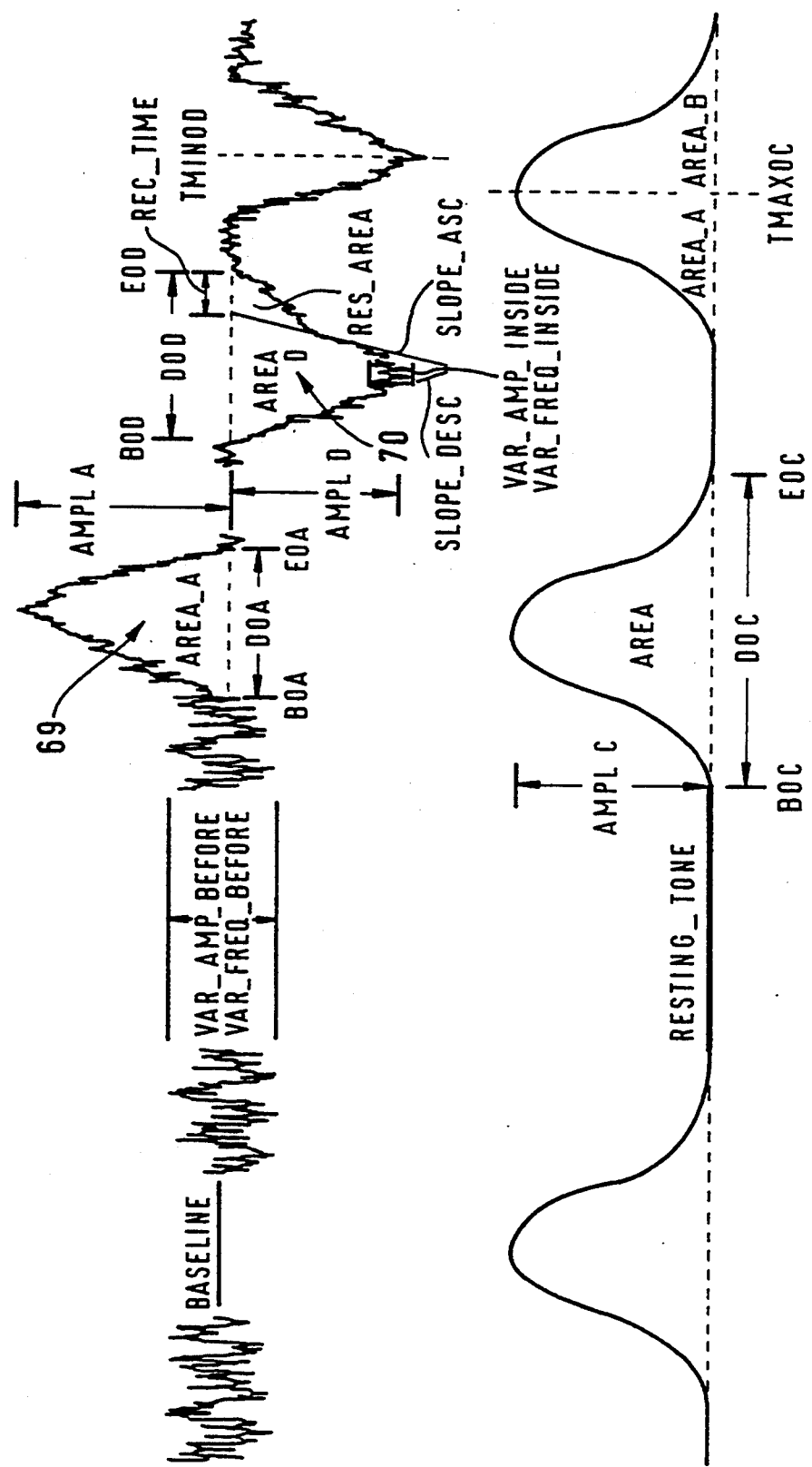
Figure 20A:
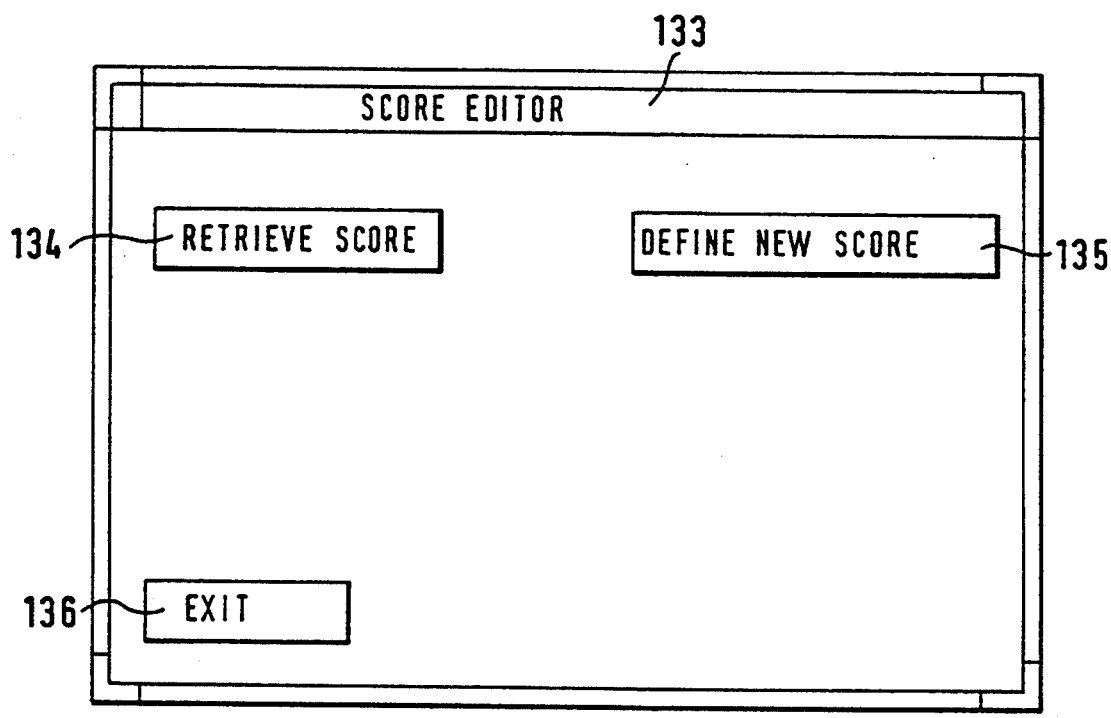
Figure 20B:
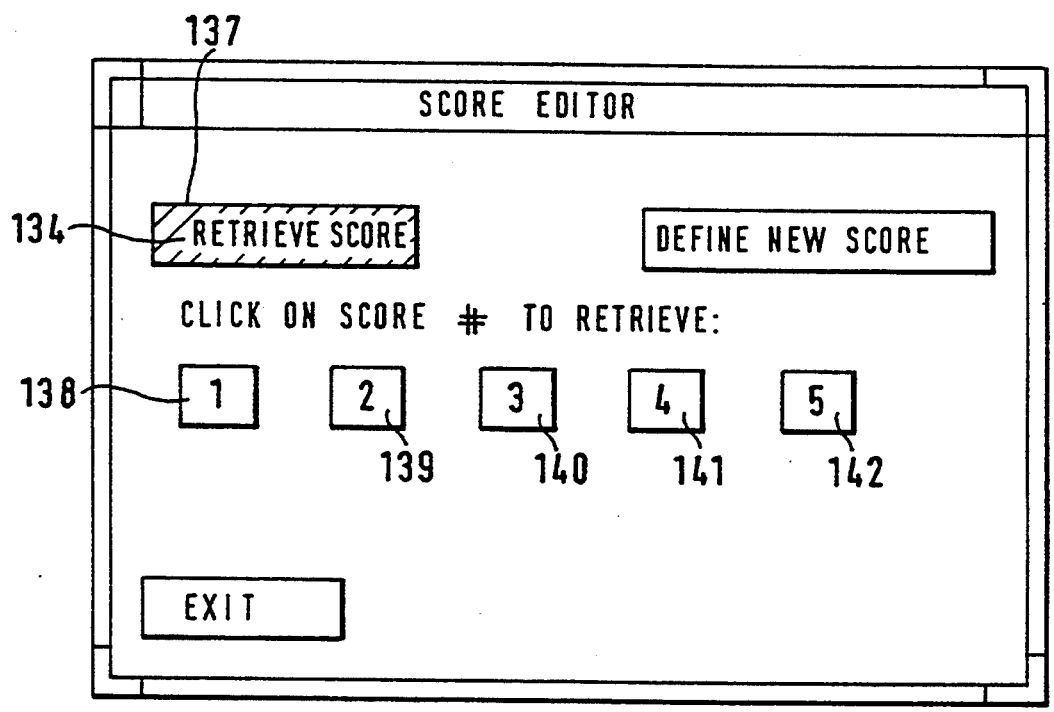
Figure 20C:
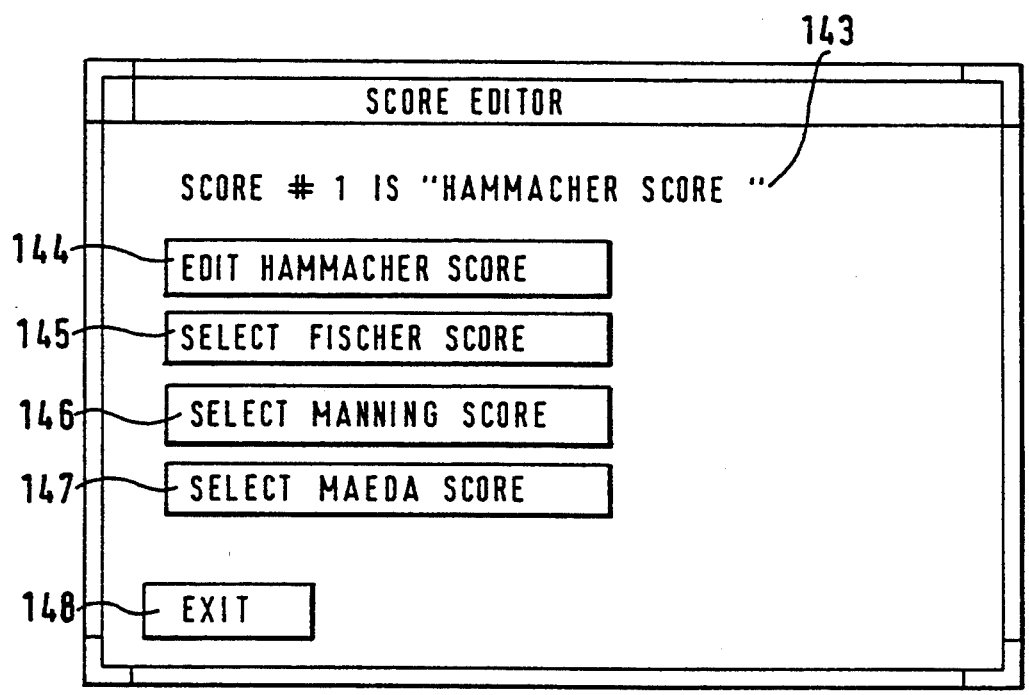
Figure 20D:
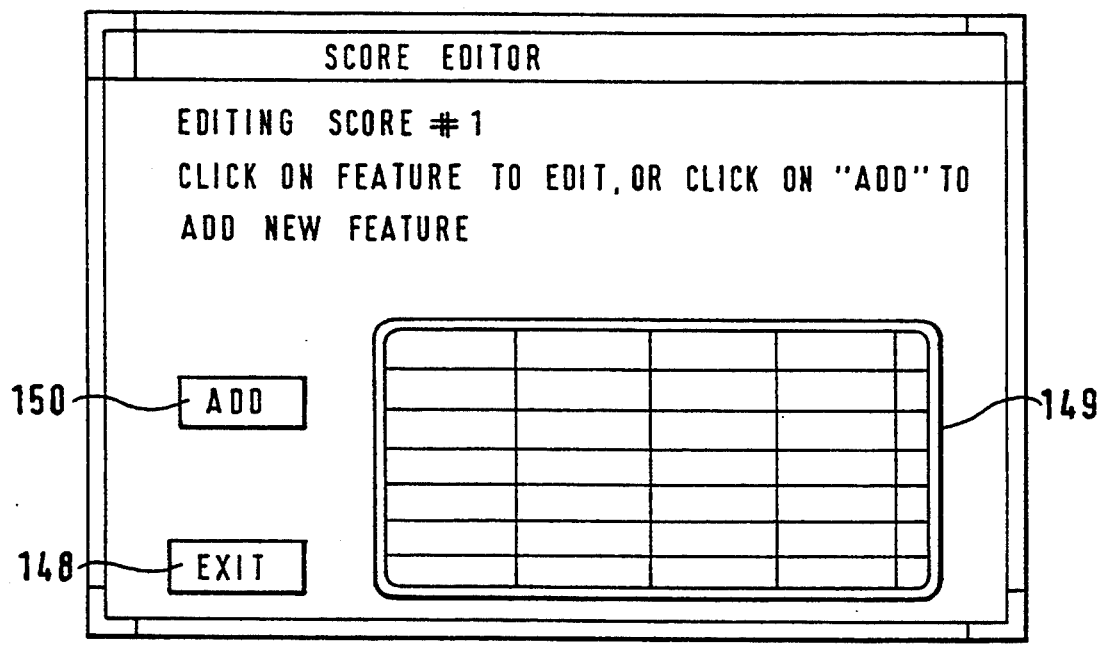
Figure 21:
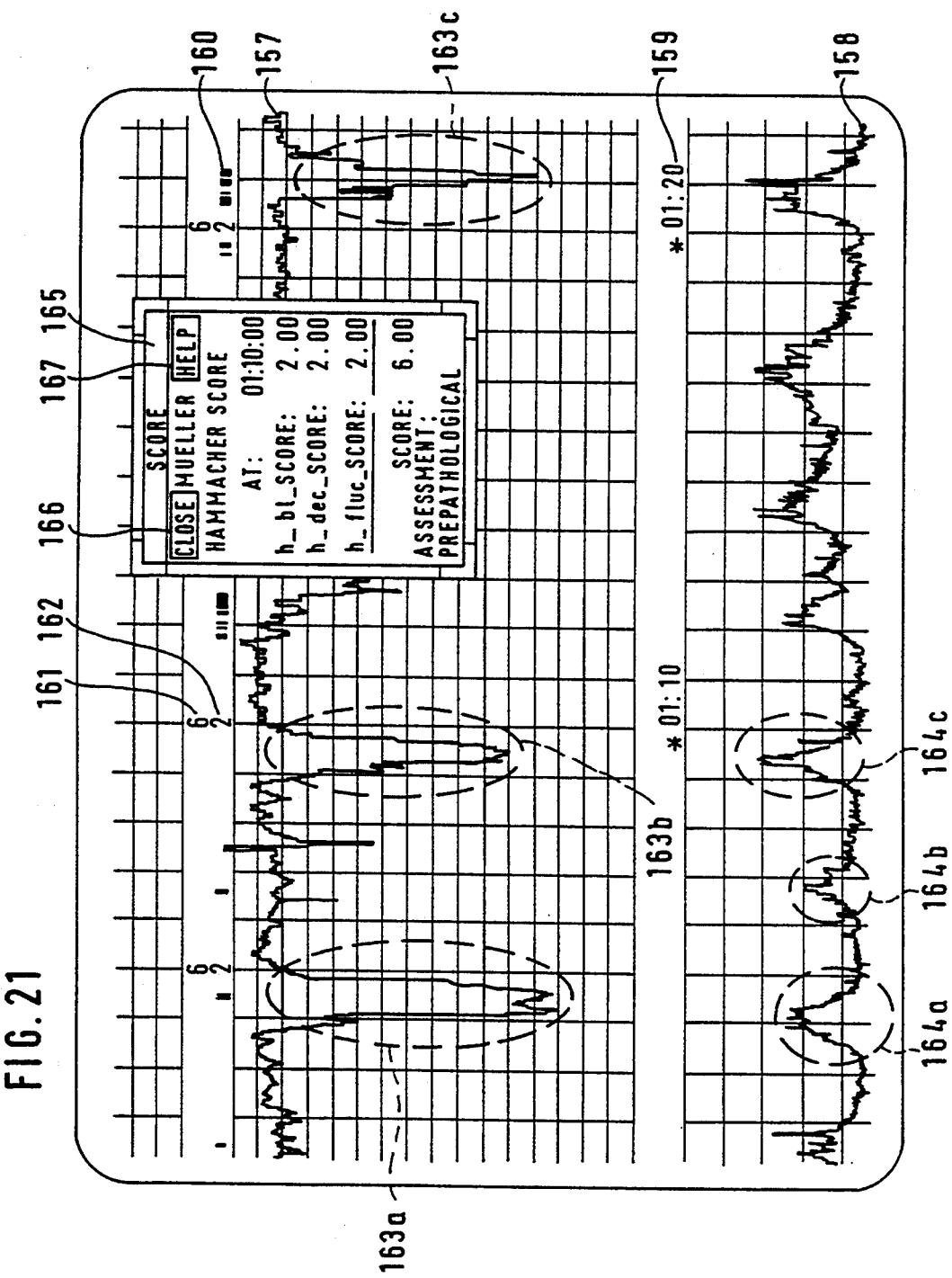
Figure 22A:
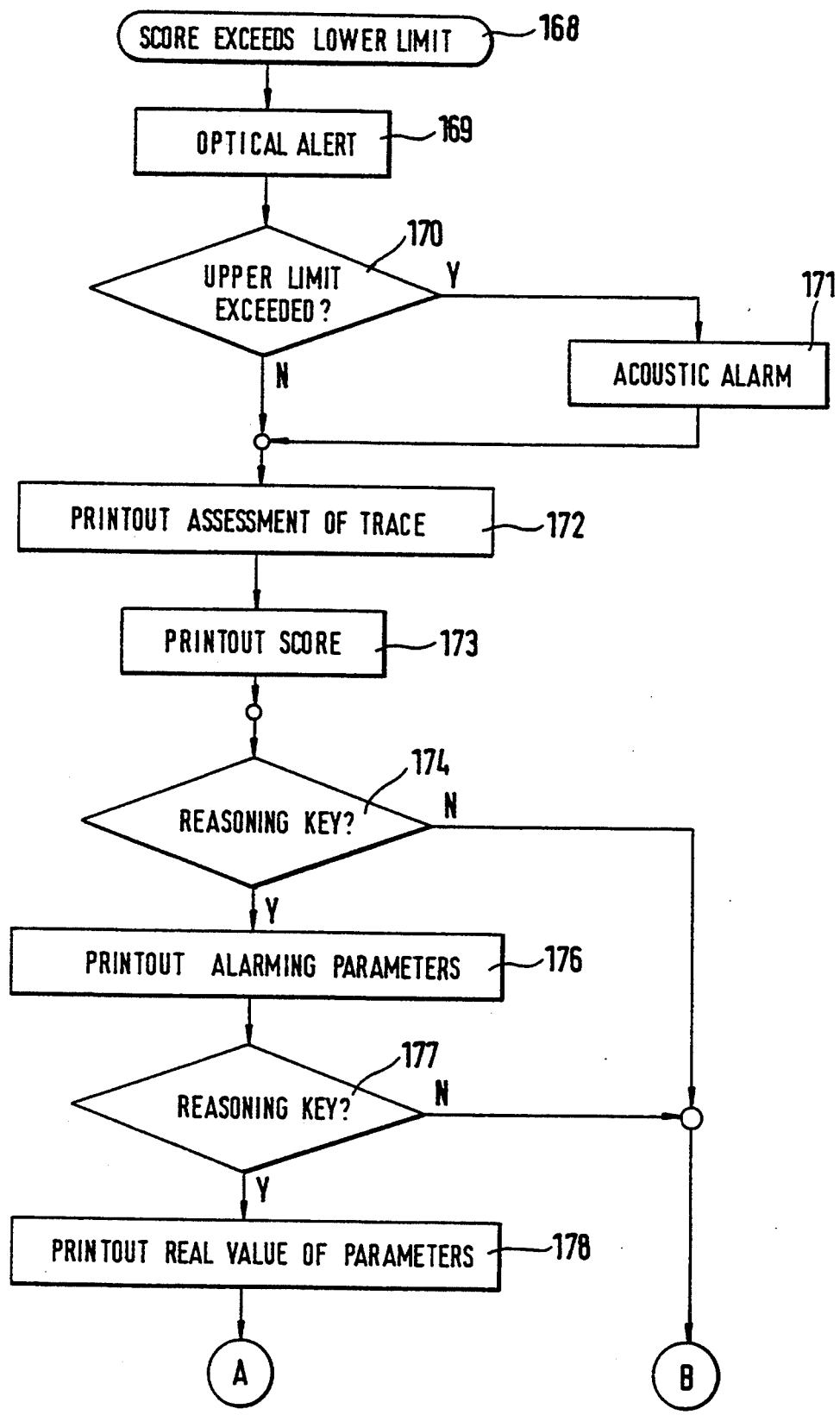
Figure 22B:
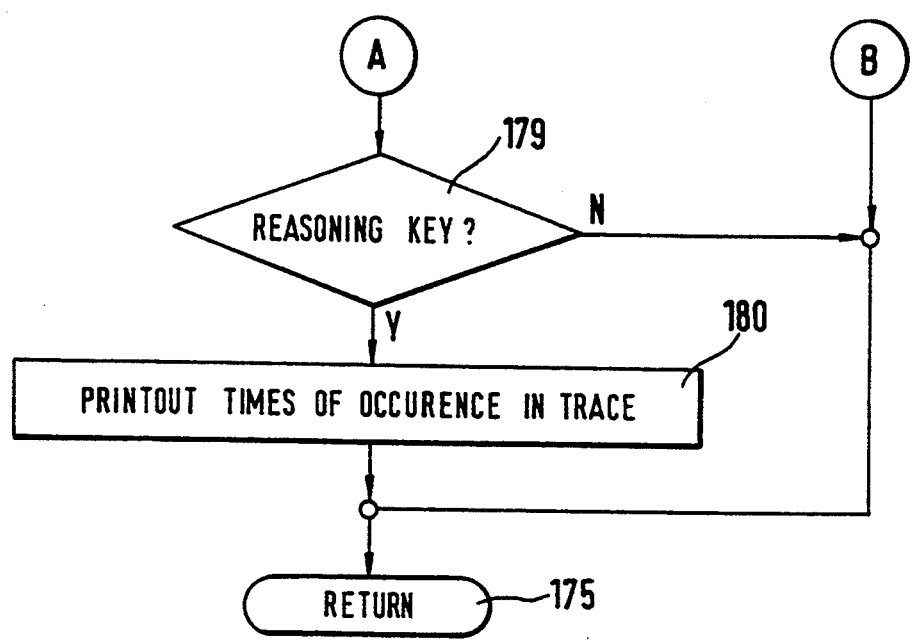

The invention will now be explained, by way of a non-limiting example, with reference to the accompanying drawings, in which:

FIG. 1 depicts a fetal monitor,

FIG. 2 is a typical configuration of the present invention using a stand-alone fetal monitor, FIG. 3 depicts another embodiment of the present invention with a multiplicity of fetal monitors connected to a central station, FIG. 4 is a block diagram showing the major components and the signal flow in a stand-alone fetal monitor, FIG. 5 is a flowchart outlining basic trace processing in an apparatus according to the present invention, FIGS. 6a and 6b depict a signal in the time domain containing a jump and its corresponding Fourier spectrum, FIGS. 7a and 7b depict the same signals as FIGS. 6a and 6b, but after removal of the jump, FIGS. 8a and 8b depict the same signals as FIGS. 7a and 7b containing a DC component, FIGS. 9a and 9b show the effect of removing the DC component in the signals of FIGS. 8a and 8b, FIGS. 10a and 10b show the signals of FIGS. 9a and 9b prior to application of a window function, FIGS. 11a and 11b illustrate the time function and the Fourier spectrum of a Hamming window, FIGS. 12a and 12b depict the effect of filtering the signals of FIGS. 10a and 10b with a Hamming window, FIGS. 13a and 13b depict the absolute spectrum and the related power spectrum after execution of a Fast Fourier Transformation (FFT), FIG. 14 depicts the spectrum of a linear digital filter for processing the spectrum of the FFT, FIG. 15 shows a corresponding exponential filter in the frequency domain, FIG. 16 is an overall diagram of the processing steps in an apparatus according to the present invention, FIGS. 17a to 17n show, by way of example, the editing process for rules, FIG. 18 is a typical cardiotocogram (CTG) trace with designation of its most important geometric features, FIG. 19 represents a "score" or alarm table, FIGS. 20a to 20d show, by way of example, the editing process for a score table, FIG. 21 shows a screen picture at a central station connected with fetal monitor(s) displaying real-time traces and a score table, FIGS. 22a and 22b are flowcharts outlining the basic operation of reasoning.

FIG. 1 depicts a prior art fetal monitor, or cardiotocograph. The fetal monitor is used to monitor the heart rate of a fetus (unborn baby) during pregnancy and labour. At the same time, the fetal monitor records uterus (or labour) activity. Simultaneous assessment of the fetal heart rate (FHR) and uterus activity (TOCO) allows a precise determination of the fetal condition.

Fetal monitor 1 comprises three jacks 2, 3 and 4 for the insertion of appropriate connectors 5, 6 and 7. These connectors are linked—via cables 8, 9 and 10—to the corresponding transducers (not shown here).

Jack 3 is an inlet for the TOCO (uterus activity) transducer. The signal measured via the TOCO channel is recorded on a thermal printer which is built-in in the monitor. FIG. 1 depicts paper 11, on which the thermal printer records the parameter traces. The TOCO recording is denoted as 12. Further, the measured TOCO value is optically indicated by means of display 13, here as a combination of 7-segment displays.

Jack 4 is an inlet for the fetal heart activity signal. Two different connectors 7 may be used: after rupture of the membranes, i.e. during second-stage labour and birth, a fetal scalp electrode can be used which is applied intravaginally. Although this method—also called "direct ECG (electrocardiogram)"—yields excellent results, it cannot be used in pre-birth applications and during pregnancy. In these cases, another transducer has to be used, namely an ultrasound (US) transducer. The ultrasound transducer emits bursts of high-frequency ultrasound waves. It further receives the ultrasound signals reflected by the maternal or fetal tissue, bones etc. In case the ultrasound bursts are reflected by moving parts of the human body, such as the valves or the walls of the fetal heart, the frequency of the reflected ultrasound waves is shifted with respect to their original frequency due to the Doppler effect. A demodulator with subsequent filters is used to obtain the Doppler signal, i.e. the signal with the Doppler frequency. Peaks in the Doppler signal are indicative of a fetal heart beat. However, as the Doppler signal is usually a quite noisy and/or disturbed signal, additional measures have to be taken to facilitate detection of a peak. The fetal monitor depicted in FIG. 1 uses an autocorrelation mechanism therefor.

In either case—i.e. regardless whether the fetal heartbeat is obtained by means of a scalp electrode or an ultrasound transducer—, the fetal heart rate is calculated as the inverse of the time interval between beat to beat, the so-called beat-to-beat heart rate. This is an important feature of fetal monitors as the beat-to-beat heart rate provides valuable-diagnostic information.

The detected fetal heart rate is displayed by means of a 7-segment display 14. Further, it is recorded on the thermal printer, see fetal heart rate trace 15. Three indicators—in the environment of FIG. 1 backlighting modules 16, 17 and 18—indicate the quality of the signal used for fetal heart rate detection. Module 16 is a red module, module 17 a yellow module and module 18 a green module. As long as the received signal is of good quality, green module 18 is on. When the signal is dubious, i.e. heartbeat detection becomes questionable, yellow module 17 is switched on, and green module 18 is switched off. Likewise, in case of a disturbed signal where no fetal beat-to-beat heart rate trace can be recorded, red LED 16 indicates bad signal quality.

Jack 7 may further provide a maternal electrocardiogram signal e.g. obtained by electrocardiogram electrodes, a plethysmographic transducer or the like. If this signal is provided, the maternal heart rate trace is also recorded, see reference number 19. The maternal heart rate may be calculated from beat to beat as well, but it is also possible to user longer time intervals than the beat-to-beat interval for maternal heart rate detection, i.e. to provide a smoother heart rate trace.

Fetal monitor 1 further provides a third jack 2 for the insertion of a corresponding connector 5. The latter is connected—via cable 8—with a second fetal transducer, namely a second fetal scalp electrode or a second ultrasound Doppler transducer. These transducers are used in case of twins to obtain a fetal beat-to-beat heart rate trace of the second fetus as well. In case a second fetal transducer is connected, the beat-to-beat heart rate of the second fetus is recorded as trace 19 instead of the maternal heart rate trace. Further, a display 20 indicates the actual value of the second fetal heart rate, and backlighting modules 21, 22 and 23 (red, yellow, green) indicate the quality of the second fetal signal.

It is understood that the fetal monitor cannot only, as depicted in FIG. 1, record two heart rate traces on the internal printer, but also three or more heart rate traces, e.g. in case that signals indicative of the heart beats of a first fetus, a second fetus and the mother are fed to the monitor. Further, the recorder is used for annotation.

Other components of the fetal monitor such as power-on button 24 will not be discussed in detail here.

A complex and time-consuming problem of fetal monitoring is the interpretation of the cardiotocogram (CTG), i.e. the diagnostic assessment of the fetal beat-to-beat heart rate trace in its interrelation to the TOCO recording. Minor differences in the two patterns may already result in a completely different diagnosis (e.g., a deceleration in the fetal heart rate which is slightly delayed with respect to a peak in labour results in another diagnosis than a deceleration which coincides with a peak in labour). Therefore, assessment of the CTG is a quite difficult and sensitive task if carried out manually, and even more complex if done automatically.

FIG. 2 depicts a first environment of the present invention, wherein the expert system is incorporated in a stand-alone fetal monitor. Reference number 25 indicates a fetal monitor of the type shown in FIG. 1 including a recorder 26 (for graphical purposes, not all details of the fetal monitor are drawn in FIG. 2).

In addition to the features of the prior art fetal monitor shown in FIG. 1, fetal monitor 25 comprises additional electronic components (e.g., an additional printed circuit board) necessary to automatically interpret or assess the CTG. Assessment is communicated to the user (physician, nurse, midwife) via recorder 26, either after each assessment or upon request. Such assessment can be the CTG score only, or alarm messages, or even more detailed information like the complete score table. Fetal monitor 25 may also contain further components like a "reasoning" key (not drawn here), as will be discussed below. In a typical environment, the CTG is assessed every 10 minutes (wherein the basis of the assessment are the data of the last 30 minutes), and the score is printed by recorder 26; if the score exceeds a certain limit, additional alarm messages are printed, and/or optic or acoustic indicators are switched on. Detailed information on the reason of an alarm, or a certain score, is only printed when a reasoning key has been pressed (see below).

In order to adapt the expert system to the specific demands of the user, fetal monitor 25 may further be connected with a personal computer 27 (via line 28). It is understood that the fetal monitor comprises the necessary interfacing hardware therefore. It is further understood that, instead of personal computer 27, a display or the like may be used (in this case, the display is driven from the fetal monitor directly, instead of using "front end" software installed in the personal computer).

If a connection between fetal monitor 25 and personal computer 27 is set up, the score tables, rules etc. of the expert system may be adapted (in a way to be described below) to the single user's needs. The revised tables, rules etc. are then stored in the expert system hardware contained in fetal monitor 25, which then operates according to the revised information. Thereafter, connection 28 is cut, so that fetal monitor 25 may operate as stand-alone unit (in fact, connection 28 is only established in order to edit the expert system's rules; fetal monitor 25 is disconnected from personal computer 27 during operation, i.e. when monitoring a pregnant woman).

It is understood that measures are provided to copy the revised rules, tables etc. of fetal monitor 25 directly to other fetal monitors, e.g. by an appropriate interface. This is particularly useful if the expert system rules are intended to be uniform in all fetal monitors in a hospital; in such case, only one editing process is necessary. The revised information of one monitor may then be copied to other fetal monitors by e.g. pressing a certain control sequence of keys which initiates the transfer of this information to another fetal monitor via appropriate interfaces and transmission lines.

FIG. 3 depicts an alternate embodiment of the present invention. A multiplicity of fetal monitors 29a to 29e are connected (transmission lines 30) with a central station 31 (here a personal computer; it is understood that this could be a minicomputer, a workstation or the like as well). The central station may control the fetal monitors of several delivery rooms or even of a hospital.

Any of fetal monitors 29a to 29e transmits its CTG data (e.g. fetal heart rates of one or two fetuses, TOCO, maternal heart rate) to central station 31. An expert system installed in central station 31 processes and assesses the various CTG data of fetal monitors 29a to 29e in distinct time intervals, e.g. every 10 minutes. The CTG traces, as well as the assessment, may be displayed on screen 31a of central station 31, or be printed on a printer 32 (or a recorder, or a plotter) which is connected with the central station. Basically, the expert system installed in central station 31 operates in a similar manner as the expert system of fetal monitor 25 (FIG. 2). A major advantage of the configuration of FIG. 3 is that messages, score tables etc. may be displayed immediately on screen 31a (e.g. in the form of windows); this is particulary helpful if reasoning is activated, i.e. the reasons for an alarm or a distinct score are requested by the user. Further, the editing process (i.e. adaptation of the expert system's rules and tables) may be performed directly on screen 31a. Last not least, the central station saves personnel, as the permanent assistance of midwives in every delivery room is not required.

Of course, it is not a strict requirement that the expert system be installed in central station 31. It is understood that fetal monitors with local expert system (like fetal monitor 25 in FIG. 2) may also be connected with a central station. In such case, the central station does not contain an expert system of its own. Instead, the remote fetal monitors process and assess the CTG data locally and transmit them (and, optionally, also their CTG assessment, e.g. the score) to the central station. Editing of the rules of the local expert systems may then be performed on the screen of the central station. A further solution is a distributed expert system (partially installed in a fetal monitor, and partially in a central station).

The major components of and the signal flow in a fetal monitor and the expert system will now be explained by the block diagram of FIG. 4. In this case, a stand-alone fetal monitor, i.e. a fetal monitor with integrated expert system, has been chosen.

The fetal monitor is generally drawn as a box 33. It is connected with a recorder 34 (which is usually integrated into the housing of the fetal monitor); instead, a display could be used as well. Two transducers are designated as 35 and 36; 35 indicates a fetal heart rate (FHR) transducer, e.g. a scalp electrode or an ultrasound transducer, and 36 indicates the TOCO (or labour) transducer, which may be of the external or internal type. Reference number 37 relates to a personal computer or similar device to edit the expert system's rules (as mentioned above, the connection 38 to personal computer 37 is not permanent, but only used during the editing process).

The signals of transducers 35 and 36 are fed, via connection lines 39 and 40, to an interfacing circuit 41. The details of such interfacing circuitry are prior art and will therefore not be described in detail here. In particular, the circuits necessary to extract the fetal heart rate from an ultrasound signal (e.g., demodulator, autocorrelator etc.) relate to this kind of interfacing circuitry. Further, certain filters (whether hardware or software filters) may be incorporated in the interfacing circuitry, e.g. a notch filter which reduces mains interference.

The signal of interfacing circuit 41 is then fed to a preprocessor 42. The preprocessor performs several measures to improve signal quality, in order to ensure reliable detection of events in the CTG. Further, it performs transformation into the frequency domain by means of a Fast Fourier Transformation (see FFT Handler 62).

Operation of preprocessor 42, inasfar as related to the processing of the fetal heart rate, will be understood from FIGS. 5 to 15. FIG. 5 depicts an overall flowchart starting with label "START" (reference number 43).

In a first box labeled as 44, preprocessing of the FHR in the time domain is performed. Such preprocessing comprises the steps of removing jumps (reference number 45), eliminating DC components (reference number 46) and applying a window function (reference number 47). The details of the various steps of time domain preprocessing will be discussed now.

The FHR received from interface circuit 41 (FIG. 4) may contain so-called (vertical) "jumps", i.e. sudden and considerable changes in the fetal heart rate. Such jumps may e.g. be caused by bad electrode contact. An example of a FHR trace containing a jump is shown in FIG. 6a. The horizontal axis of this diagram represents time; in this case, as the FHR is sampled in the fetal monitor resulting in a discrete function in time, several samples i in time have been drawn, $0<i<551$. (The samples are related to real time by the relation $t=i*\Delta T$, wherein $\Delta T$ is the sampling period). The vertical axis depicts the fetal heart rate samples $tr_i$ in bpm (beats per minute), $50<tr_i<160$.

It will be observed that the FHR trace contains a considerable negative vertical jump (reference number 48) from approx. 115 bpm to approx. 60 bpm and a corresponding positive vertical jump (reference number 49). Such jumps impact the FHR signal, and consequently its subsequent assessment, considerably. This applies particularly for the assessment in the frequency domain. The occurrence of a jump in the time domain corresponds to the overlay of an si-function (sin x/x) to the original spectrum. The weight of the si-function is proportional to the height of the jump.

This is illustrated by FIG. 6b which depicts the discrete fourier spectrum of the function of FIG. 6a. The horizontal axis represents the discrete frequency k, $0<k<32$, and the vertical axis the amplitude $|F_k|$ of the fourier components. The overlayed si-function is indicated by dashed line 50. It will be appreciated that the si-function contributes in particular to the low-frequency components. As the subsequent assessment of the FHR trace is partially based on its components in the frequency domain, it will be appreciated that the components created by the jump will partially distort the spectrum and therefore may lead to inappropriate diagnosis.

Therefore, it is of clinical advantage to remove the vertical jumps in the FHR time trace. This is performed in box 45 (FIG. 5). The difference between two subsequent FHR samples is compared with a predefined, adaptive or adjustable limit, and if this limit is exceeded, it is identified as a "jump" and thus removed from the trace. Preferably, the limit is L=15 bpm, such that a jump is identified when $$|tr_{i+1} - tr_i| > 15 \text{ bpm.} \quad (1)$$

Removal of the jump may be performed by subtracting the amplitude of the jump from the sample upon which the jump has been noted, and from all future samples. For example, if in the trace of FIG. 6a the difference between two subsequent samples dump at reference number 48) is $$tr_{i+1} - tr_i = 60 \text{ bpm} - 115 \text{ bpm} = -55 \text{ bpm} \quad (2a)$$

$$(|-55 \text{ bpm}| = 55 \text{ bpm} > 15 \text{ bpm, i.e. limit exceeded}), \quad (2b)$$

the difference of −55 bpm will be subtracted from the amplitudes of all future samples, i.e.

$$tr_i^* = tr_i - (-55 \text{ bpm}) = tr_i + 55 \text{ bpm} \quad (3)$$

It has to be noted that the above subtraction has to be made for all future samples. In the example of FIG. 6a, the second jump (reference number 49) compensates for the first jump, so that no correction is necessary after the second jump.

The result of jump removal is depicted in FIG. 7a. The corresponding spectrum in the frequency domain (FIG. 7b) shows that the si-function, in particular their low-frequency components, have been removed.

The second step of time domain processing (FIG. 5) consists in the removal of the direct component (box 46). This makes further processing, e.g. area calculations, easier. For this purpose, either a constant, or (preferably) a long-term average of the FHR trace is subtracted from the actual trace. It is also possible to pass the FHR trace through a low-pass filter with long time constant (in mathematical terms, this this is an equivalent to the subtraction of a constant); the time constant may also be adaptive.

The process of DC removal is illustrated by FIGS. 8a to 9b. FIG. 8a depicts the FHR trace in time prior to DC removal, and FIG. 8b its spectrum (in effect, these figures are identical to FIGS. 7a and 7b, but drawn repeatedly to illustrate the effect of. DC removal, i.e. the status prior to and after DC removal, on a single page).

FIGS. 9a and 9b show the trace in time, and the associated Fourier spectrum, after DC removal. The samples in time have been denoted as $tm_i$ (instead of $tr_i$, as in FIG. 8a). They are now evenly distributed around the horizontal zero A problem of Fast Fourier Transformation is that, due to the limited duration (in time) of the original signal (which corresponds to a multiplication with a rectangular window), spectral "leakage" is observed, i.e. the frequency maximum is broader than that of the unlimited original signal, and secondary maxima occur which are not present in the unlimited original signal. In order to suppress or reduce the effects of spectral leakage, the time trace of the FHR is multiplied with a window function. Preferred window functions are the Hamming window ($\frac{1}{2}(1-\cos(2\pi k/N))$) or the Interim Data window (Tukey).

Box 47 (FIG. 5) relates to the appliance of a window function. The effect is illustrated in FIGS. 10a to 12b.

FIGS. 10a and 10b show the time trace and the Fourier spectrum of the FHR after DC elimination, but prior to application of a Hamming window (these figures correspond to FIGS. 9a and 9b). The time response of the Hamming window is depicted in FIG. 11a, $\omega_i$ being its amplitude; likewise, its frequency response is depicted in FIG. 11b, $|F\omega_k|$ indicating the amplitude in the frequency domain. It will be noted that, due to the cosine function, the spectrum of the Hamming window is very small.

The FHR signal of FIG. 10a and the Hamming window function of FIG. 11a are subject to convolution in the time domain (which corresponds to a multiplication of their spectra in the frequency domain). The resulting time and frequency responses, $t_i$ and $|F_k|$ are shown in FIGS. 12a and 12b. It will be noted that several high-frequency components of FIG. 10b, which correspond to secondary maxima, have been attentuated considerably in the spectrum of FIG. 12b.

Returning to FIG. 5, the above steps describe the processing of the FHR trace in the time domain (box 44). Processing proceeds now with transformation into the frequency domain. First, the preprocessed FHR time trace is subject to Fast Fourier Transformation (FFT, box 51). Preferably, a Fast Hartley Transformation (FHT) is used for this purpose, wherein the Fourier coefficients of interest are derived from the even and odd parts of the Hartley values. The result is the absolute spectrum of the $|F_k|$ values, depicted in FIG. 13a, and the power spectrum, i.e. the spectrum of the power coefficients $P_k$ (FIG. 13b).

Box 52 in FIG. 5 further indicates the appliance of a filter function in the frequency domain, i.e. the multiplication of the obtained spectra with the coefficients of the filter. The filter reduces the low frequency components of the spectrum, which is useful to derive the amplitude and frequency of FHR variability. In turn, amplitude and frequency of the FHR variability are important parameters for the evaluation and the "scoring" (e.g. Hammacher score) of the CTG.

A first preferred filter function is depicted in FIG. 14. This is a linear filter. Its characteristics may be adapted to local requirements by appropriate selection of the values for the amplitude offset, "filterOval", and its width "filterwidth". The fetal monitor offers default "filterOval" and "filterwidth" values, which may be adapted by the user to his specific requirements, in a manner similar to the editing processes described below. In the example of FIG. 14, "filterOval" has been selected as $I_o=0.5$, and "filterwidth" as k=10. This results in a frequency response with reference number 53. $I_k$ are the filter coefficients in the frequency domain, i.e. the frequency amplitudes.

An alternate filter function, namely an exponential filter, is depicted in FIG. 15. The coefficients of this filter are $$e_k = (1 - \text{filterOval}) * \left[1 - \exp\left[\frac{-k}{\text{filterwidth}}\right]\right] + \text{filterOval} \quad (4)$$

As in the case of the linear filter, the user may either use the default values for "filterOval" and "filterwidth", or his own ones.

An example of the exponential filter for filterOval:=0.33 and filterwidth:=10 is drawn in FIG. 15.

The next step in the diagram of FIG. 5, after appliance of the filter function, is to calculate the frequency and the amplitude of the FHR variability. It is well known in the art that one of the clinically most important parameters of the fetal heart rate is its variability, i.e. the amplitude and frequency of medium-range fluctuations (in the range of approx. 2–6/min, in contrast to the baseline level <2/min and the fast oscillations >6/min, cf. Hammacher, "Einführung in die Cardiotokographie", Böblingen 1978).

According to the present invention, information on FHR variability is obtained in the frequency domain. This information is generated on a short-intervallic basis, i.e. not in longer time intervals (as the assessment of the CTG).

Two characteristics are important for FHR variability. The first is its frequency which is searched for in the FFT spectrum (box 54 in FIG. 5) as the spectral line with the maximum amplitude, i.e.

$$f_{VAR} = \max (F(i\Delta\omega))|_{i=m}^{M} \quad (5)$$

wherein $F(i\Delta\omega)$ denotes the amplitude of the single spectral lines, have the frequency spacing between subsequent samples, m is the index of the lowest spectral line regarded, M is the corresponding highest index, and $f_{VAR}$ is the frequency of FHR variability. Low frequency components, i.e. spectral lines, have already been suppressed in the preceding filtering step (box 52).

Similarly, in box 55 of FIG. 5, the amplitude of FHR variability is calculated as $$A_{VAR} = C * \sum_{i=m}^{M} |F(i\Delta\omega)| \quad (6)$$

Note that, as the frequency of FHR variability is not restricted to a single spectral line (and may even be subject to slight changes, which is reflected by a small spectral leakage, as the regarded time interval is not infinitesimally small; i.e., due to the time interval regarded when performing the FFT, a frequency change of the FHR variability occurring during that time interval results in leakage of the associated spectral line). Therefore, the above formula (6) sums the amplitudes of several spectral lines in the environment of the maximum line (limits m, M in formula (6) are not identical to limits m, M in formula (5)).

It is possible to sum simply the amplitudes of a certain amount of spectral lines in the environment of the maximum line, e.g. from i=−3 to i=+3. The amount of spectral lines to be taken into account may also be user-configurable. Instead, and more advantageously, only sidelobes with a certain amplitude, e.g. >80% of the maximum lobe, are taken into account. The frequency boundaries of the medium-range fluctuations, e.g. 2/min and 6/min, may be used in order to prevent the addition of sidelobes in another frequency band, or with an amplitude which exceeds the amplitude of the main lobe. Alternatively, the number of sidelobes (secondary maximum) to be taken into account may be specified.

C is a scale factor.

The amplitude and frequency of FHR variability is then stored in a spectral characteristics buffer (box 56) for further evaluation. That is, the later assessment of the CTG is, among other, based on a time trace of the frequency and amplitude of FHR variability and can thus be evaluated for certain statistical criteria (see below). The "time window" for calculating frequency and amplitude of FHR variability (i.e. the number of samples taken for executing the FFT) is usually around 1 minute, but may be adapted by the user to his specific needs (see also below).

Further spectral characteristics may be calculated which are of importance for evaluating the CTG, e.g. frequency and amplitude of the baseline variability (lower than 2/min) or of high-frequency oscillations (>6/min). These calculations have not been shown in detail in the diagram of FIG. 5. However, the results of these calculations may be stored in spectral characteristics buffer 56 as well, like the Fourier spectrum itself.

Operation of the preprocessor stops at "RETURN" label 57. The preprocessor may now perform other tasks and start the routine of FIG. 5 again later.

For the purpose of further processing, as well as recording and/or display, the FHR trace in time is also fed from preprocessor 42 to a real time wave buffer 58. This may be the original time trace as entered into box 44, or the time trace after removal of the jumps, depending on the needs of the specific application.

Further, trend information is generated. This is compressed information on the time trace, e.g. in the form of a histogram, which may be invoked (printed, displayed) by the physician in case he wants to know the reasons for an alarm or a certain CTG assessment, or if he simply wants information in case he has been absent for a longer time period.

For this purpose, a data compressor 59 is provided. It extracts the major characteristics of the time trace and stores them in trend buffer 60, for the purpose of later processing and recording.

The outputs of real time wave buffer 58, as well as of trend buffer 60, are fed to an interface 61, which, in turn, is connected with recorder 34.

In equidistant time intervals, the fetal monitor performs an assessment of the cardiotocogram, i.e. of the fetal heart rate in relation to the TOCO recording. Typical time intervals are 10 minutes, wherein the assessment of the CTG is based on its characteristics (time and frequency) of the last 30 minutes. However, the intervals of assessment, as well as the time window taken for the assessment, may be adjustable. Further, assessments may be produced in case special conditions occur, or upon request (e.g. pushing of a button) of the user.

Assessment is made in several steps. For this purpose, a trace processor 63, a validation processor 64, a classification processor 65, a statistics processor 66 and a score processor 67 are provided. Operation of these processors will now be explained in detail.

Trace processor 63 serves basically four tasks:

1. First, it uses the output of preprocessor 42, i.e. the contents of real time wave buffer 58, trend buffer 60 and spectral characteristics buffer 56 to generate several mathematical expressions which describe the baseline of the FHR.

Such may e.g. be the level or the variability of the baseline. The baseline level is the mean value of the FHR, calculated with a long (preferably adjustable) time constant. It can be used to classify the FHR as normal, bradycardic or tachycardic.

Evaluation of the baseline variability consists of the calculation or determination of several characteristics of the FHR. These are primarily:

a) The amplitude of the micro fluctuation, i.e. of the beat-to-beat variation, including the determination of minimum and maximum, and calculation of statistical expressions such as standard deviation etc. over a selectable time range.

b) The amplitude of the macro fluctuation and determination of the period(s) of time during which this amplitude remains in one of n selectable ranges. Ranges could e.g. be <5 bpm, 5–10 bpm, 10–25 bpm and >25 bpm, corresponding to a classification of the FHR as silent, undulatory, limited undulatory and saltatory. Such amplitude is determined from the spectral analysis, i.e. by investigating the spectral components of the Fourier-transformed FHR.

c) Correspondingly, the frequency of the macro fluctation may be determined. This analysis also uses the spectrum and determines period(s) of time during which the frequency is in one of n selectable ranges, e,g. <1/min, 1–2/min, 2–5/min, 5–6/min and >6/min.

d) Last not least, the macro fluctuation may then be classified according to type and time. Likewise, a time compressed trend of amplitude and frequency of the macro fluctuation may be generated and stored in trend buffer 60 (cf. arrow 68).

Sinusoidal oscillations may also be detected and quantized using the Fourier spectrum. This is extremely valuable diagnostic information.

The results of the calculations are temporarily stored and used later for the final assessment of the CTG; in part, they also serve as inputs for statistics processor 66.

2. Second, trace processor 63 looks for accelerations in the fetal heart rate trace. For this purpose, several parameters are calculated which may then be used to classify a certain period of the FHR as "acceleration".

Typical and preferred parameters are:

a) Area under a suspected acceleration, i.e, between begin of acceleration (BOA) and end of acceleration (EOA). The specific meaning of these (and some of the following) abbreviations are illustrated in FIG. 18 which depicts, in its upper trace, an example of an FHR reading, and in its lower trace an example of a TOCO reading. Reference number 69 in this figure illustrates a typical acceleration with area AREAA. BOA is the begin of the acceleration, EOA its end and DOA its duration.

b) Duration (DOA) of a suspected acceleration, by identifying its begin (BOA) and its end (EOA).

c) Amplitude of the acceleration, i.e. the maximum of the FHR and its difference to the calculated baseline (designated as "AMPLA" in FIG. 18).

3. Likewise, decelerations are identified in the fetal heart rate trace. Preferred parameters for identification of a deceleration are:

a) Amplitude (difference of the minimum of suspected deceleration to the baseline). In the deceleration 70 depicted in FIG. 18, this amplitude has been designated as "AMPLD". A time compressed version may also be sent to trend buffer 60.

b) Total duration ("DOD"=duration of deceleration in FIG. 18), i.e. the time between begin of deceleration BOD and end of deceleration EOD. The result is stored for further processing; a time compressed version is sent to trend buffer 60.

c) Recovery time ("REC_TIME" in FIG. 18). The ascending branch of the deceleration ("SLOPE_ASC") is approximated by a straight line, and the point in time where this straight line crosses the baseline is calculated. The time between this "artificial" point in time (i.e. the point in time when zero-crossing of the FHR could be expected) and the point in time when the FHR actually reaches the baseline ("EOD") is the recovery time. Apart from preliminary storing, a time compressed trend of the recovery time, as well as of the recovery time per deceleration area, is sent to trend buffer 60.

d) Total area under the deceleration ("AREAD" in FIG. 18), i.e. area between FHR trace and baseline, between BOD and EOD. Time compressed trend of area is sent to trend buffer 60.

e) Residual area. This is the total area between the baseline and actual FHR trace from "expected EOD" to actual "EOD" (outlined as "RES_AREA" in FIG. 18). Stored and time compressed trend is sent to trend buffer 60.

f) Slope of descending part ("SLOPE_DESC"). This is the slope (i.e. an approximated straight line) between "BOD" and the point where the FHR has reached 80% of its minimum. The slope may then be classified. Compressed trends of the slope and its classification are sent to trend buffer 60.

g) Latency time between the begin of a contraction ("BOC") in the TOCO channel and the begin of a deceleration ("BOD") in the FHR channel. The latency time is not expressly indicated in FIG. 18. A time compressed trend of the latency time is sent to trend buffer 60.

h) Lag time, i.e. the time between the maximum of a contraction in the TOCO channel and the minimum of a deceleration ("AMPLD") in the FHR channel. The lag time is not expressly indicated in FIG. 18. A time compressed trend of the lag time is sent to trend buffer 60.

4. The fourth task of trace processor 63 is to identify possible contractions in the TOCO channel. Preferred parameters for identification are:

a) Resting tone (identified as "RESTING_TONE" in FIG. 18), i.e. the baseline of the TOCO channel.

b) Amplitude of contraction ("AMPLC" in FIG. 18), i.e. the maximum of a suspected contraction over baseline RESTING_TONE. In order to determine a reliable amplitude, possible artifacts (e.g. caused by breathing) have to be removed.

A mean value, namely the mean of the amplitudes of contractions over a prescribed time period (e.g., 10 minutes), may also be calculated. A time compressed trend of this mean value, and of the actual amplitude, is stored in trend buffer 60.

c) The time between the onset of a contraction and its maximum ("TMAXOC" in FIG. 18), as well as the area under the TOCO trace between these points in time (labeled as "AREA_A" in FIG. 18).

d) In similar manner, the time between the maximum of a contraction and the end of this contraction may be calculated, as well as the area under the TOCO trace between these points in time ("AREA_B" in FIG. 18).

e) Last not least, the complete area under a contraction, that is AREA_A+AREA_B.

With reference to FIG. 18, the following is a complete list of abbreviations used for the FHR trace in the upper channel and the TOCO trace in the lower channel:

| | |
|---|---|
| BASELINE | DC value of FHR trace |
| VAR_AMPL_BEFORE | Amplitude of the FHR variability prior to occurence of an acceleration or deceleration |
| VAR_FREQ_BEFORE | Frequency of the FHR variability prior to occurence of an acceleration or deceleration |
| BOA | Begin of acceleration |
| EOA | End of acceleration |
| DOA | Duration of acceleration |
| AREAA | Area under acceleration |
| AMPLA | Maximum amplitude of acceleration |
| BOD | Begin of deceleration |
| EOD | End of deceleration |
| DOD | Duration of deceleration |
| AREAD | Area under deceleration |
| AMPLD | Maximal amplitude of deceleration |
| SLOPE_DESC | Falling slope of deceleration, approximated by straight line |
| SLOPE_ASC | Ascending slope of deceleration, approximated by straight line |
| VAR_AMP_INSIDE | Amplitude of FHR variability during minimum of deceleration |
| VAR_FREQ_INSIDE | Frequency of FHR variability during minimum of deceleration |
| REC_TIME | Time delay between the point where straight line SLOPE_ASC crosses the baseline and the point in time when the FHR actually reaches the baseline again |
| RES_AREA | Area between FHR, SLOPE_ASC and BASELINE |
| TMINOD | Minimum delay time between onset of deceleration and its maximum |
| RESTING_TONE | DC value of TOCO trace |
| BOC | Begin of contraction |
| EOC | End of contraction |
| DOC | Duration of contraction |
| AMPLC | Maximum amplitude of contraction |
| AREA | Total area between contraction and RESTING_TONE |
| AREA_A | Area between begin of contraction, its maximum and RESTING_TONE |
| AREA_B | Area between maximum of contraction, its end and RESTING_TONE |
| TMAXOC | Maximum delay time between onset of contraction and its maximum |

It is understood that mathematical characteristics other than those explicitly shown in FIG. 18 may be used as criteria as well, e.g. the time delay between a contraction in the TOCO trace and a deceleration in the FHR trace.

It has to be outlined that operation of trace processor 63 is very sensitive, i.e. the trace processor will classify as many as possible patterns as accelerations, decelerations or contractions. This means, on the other hand, that the trace processor is not very selective. The purpose of this strategy is not to miss any acceleration, deceleration or contraction—in the first step performed by the trace processor, as many as possible patterns are identified as accelerations, decelerations and contractions, whereas in a second step, performed by validation processor 64 (see below), only those of interest are "filtered". As the operating rules of the validation processor are adaptable (see also below), the sensitivity of the fetal monitor for accelerations, decelerations and contractions may be "tuned" to the specific user's needs.

It should be outlined here that all (or at least the majority of) operating rules of trace processor 63 are provided by an expert system. Basically, the expert system offers at least one default set—preferably, a selection among several default sets—of operating rules. However, via an appropriate expert system interface (e.g. personal computer 37), those rules may be edited, i.e. changed, or even new rules may be defined. This process will be described in detail below, according to the rules for classification processor 65 (which uses a multiplicity of user definable rules). However, even trace processor 63 works according to some changable rules, e.g. the length of the "time window" for calculating the baseline parameters.

The concept of the invention is also illustrated, in a more sketchy way, in the diagram of FIG. 16. This diagram depicts the basic features and characteristics of the single processing elements, as well as signal flow in the present invention.

The rough CTG is outlined as 71 in this figure. First of all, it is subject to algorithmic parameter extraction (box 72). This is effectively the task performed by trace processor 63. The trace processor operates under control of a rule interpreter 73.

The rules of a rule interpreter 73 may be edited via a rule editor. In the depicted example, this is a graphical interactive expert interface 74. The rules concerning algorithmic parameter extraction are the so-called "parameter settings" (box 75). As outlined above, these rules may be edited; on the other hand, they control rule interpreter 73 and thus (arrow 76) operation of the algorithmic parameter extraction 72.

Box 72 generates rough (i.e., unqualified) information about the baseline parameters (77), accelerations (78), decelerations (79) and contractions (80). One will note that these are exactly the tasks of trace processor 63 in the environment of FIG. 4.

The outputs of "pots" 77-80 are fed to rule based pattern validation (box 81). In this step, so-called "valid contractions" (reference number 82) are selected from the multiplicity of candidates for contractions, as provided by "pot" 80. A valid contraction is a contraction which fulfils several additional criteria. These criteria are provided as a standard or default set of rules in the expert system (preferably, there are even several selectable standards); however, even these criteria or "rules" are user changable or definable. "Pot" 83 represents said criteria, which may be edited (or additional criteria may be introduced) by expert interface 74; on the other hand, they control operation of rule interpreter 73, and thus operation of rule based pattern validation 81 as well.

Box 81 further generates validated (or valid) decelerations 84 (from the "rough" decelerations in "pot" 79), valid accelerations 85, the baseline average 86 and the baseline variability 87.

The remaining components in FIG. 16 will be discussed later. It should be noted that arrow 88 indicates the direction of CTG interpretation, and arrow 89 the direction of expert interpretation control.

Returning now to FIG. 4, validation processor 64 performs the task of rule based pattern validation in FIG. 16, i.e. it selects those of the possible candidates for accelerations, decelerations and contractions identified by trace processor 63 which fulfill certain criteria and may therefore reliably regarded as events.

The criteria or rules may e.g. be a minimum duration of a deceleration or a contraction, a minimum amplitude, a minimal or maximal area or the like. As already mentioned, these rules may be adapted to a specific required environment or application under expert control. For this purpose, validation processor 64 cooperates with a rule memory 90 (connection 91) containing the actual (and possibly alternate) set(s) of rules. A typical rule for identifying a valid contraction may e.g. be if DOC>25 and AREA>150 then
  CONTRACTION is VALID (DOC=duration of contraction, AREA=area between contraction and resting tone, cf. FIG. 18).

The contents of rule memory 90 may be edited by an expert. For this purpose, it is connected with an expert interface 92 (e.g. a processor generating graphical overlay information), which, in turn, is connected via interface 93 with personal computer 37. By the way, the rules of trace processor 63 may be edited in a similar manner (connection 94).

The output of validation processor 64 is connected with classification processor 65 which classifies the events recorded by the preceding stages according to their diagnostic meaning. AS a simple example, a deceleration may be classified as "late" with respect to a preceding contraction, which is valuable diagnostic information.

To some extent, operation of the classification processor 65 is the "heart" of CTG interpretation, as this is the basis for diagnostic assessment of the fetal condition, and thus has considerable consequences for therapy (e.g., decision on a section, i.e. a Caesarean section). Its rules are subject to editing, see arrow 97.

Detailed examples for classification are:

An acceleration may particularly be classified according to its type, its amplitude (in n classes) and its duration (in m classes). In turn, typical type classifications are:
  periodical—i.e. synchronous with contractions,
  nonperiodical
  initial—i.e. before deceleration,
  compensatory—i.e. after deceleration, sporadic,
etc. The possible types, and the rules identifying those types, are stored in rule memory 90. A typical criterion for periodic accelerations would e.g. be that the time shift between accelerations and contractions does not exceed a certain limit.

The results of the classification are temporarily stored; a compressed version is also sent to trend buffer 60.

Likewise, the decelerations may be classified according to their type, their amplitude (in n classes) and their duration (in m classes). Typical classifications of types of decelerations are:
  late,
  variable,
  early,
  prolonged,
  sporadic,
  periodic,
  late variable,
etc. A compressed version of the deceleration classification is also sent to trend buffer 60.

As in the case of the accelerations and decelerations, the contractions may be classified according to their amplitude (in n classes) and duration (in m classes), as well as their type. Typical types are:
  TYPE 1 (AREA_A>AREA_B, see FIG. 18),
  TYPE 2 (AREA_A=AREA_B),
  TYPE 3 (AREA_A>AREA_B),
  small,
  normal,
  hyperstolic,
  strong,
  oscillating,
etc. A typical rule for identifying a TYPE 1 (valid) contraction is e.g.

if AREA_A>(AREA_B+10) THEN
  CONTRACTION IS TYPE_1

Further examples for classifying the type of contraction are:

if AREA_A=(AREA_B+/−10) then
  CONTRACTION is TYPE_2 if AREA_A<(AREA_B−10) then
  CONTRACTION is TYPE_3 if AMPLC<60 then CONTRACTION is
  NORMAL if AMPLC>=60 then CONTRACTION is
  STRONG It will be appreciated that such rules may be edited, e.g. by changing the qualifters or numeric values, or even by adding new rules. For example, the limit for classifying a contraction as strong could be altered from 60 to 70. Actual editing examples will be given below.

Classification processor 65 further classifies the variability of the heart rate, also according to its amplitude and frequency (assigned to classes) and according to the type, e.g. as
- silent,
- undulatory,
- saltatory,
- sleeping,
- awake,
- stressed etc. Further, fetal movement may be detected.

It is understood that time compressed trends of the contraction and variability classification are sent to trend buffer 60 as well.

In FIG. 16, the tasks of the classification processor are depicted by box 95 which relates to rule based classification. The classification rules as such (which are subject to expert editing) are indicated by "pot" 96.

The output of the classification process is, by way of example, indicated by "pots" 98a–98d, 99a–99c and 100a–100c. 98a contains contractions classified as "normal", 98b contractions classified as "Type 1", 98c contractions classified as "Type 2" and 98d contractions classified as "Type 3". Likewise, 99a contains accelerations classified as "sporadic"; the accelerations in 99b and 99c have been classified as "initial" and "compensatory", respectively. In similar manner, pots 100a to 100c contain classified variabilities: 100a="silent", 100b="normal", 100c="saltatory". It will be appreciated that the classifications drawn in FIG. 16 are, for graphical purposes, only some exemplary classifications; Other classifications, as well as the classification of the decelerations, are available (see the above lists), but not drawn here.

For the purpose of illustration, establishment of a new rule will now be explained with reference to FIGS. 17a to 17n. FIG. 17o depicts the invocation of an existing rule prior to editing. Although this example describes the process of creating and modifying the rules relating to classification processor 65, it will be appreciated that the rules controlling operation of trace processor 63 and validation processor 64 may be edited in a similar manner.

To begin creating a new rule, the expert (which may be the supervising physician in a hospital) invokes a menu on personal computer 37 (as mentioned above, for the purpose of editing the rules in a stand-alone fetal monitor, it may be necessary to connect the fetal monitor with a personal computer, display or the like). Control of the expert interaction, and invocation of menus, may either be performed by a program in personal computer 37, or by appropriate control instructions from expert interface 92.

FIG. 17a depicts the menu appearing on the screen of personal computer 37. The Rule Editor (reference number 101) offers the possibility to define a <pattern> (ref. no. 102) as being of <pattern type> (ref. no. 103) if a <condition> (ref. no. 104) is true. Further, it offers invocation of an existing rule (ref. no. 105) or acceptance ("write") of a built or edited rule (ref. no. 106).

Now let us assume that a new rule is to be created, i.e. the conditions of a rule have to be set up. The expert activates field 102, i.e. <pattern>. This may be done by moving a cursor to field 102 and pressing a key like the RETURN key on a keyboard, by moving a cursor with a computer mouse to field 102 and clicking the mouse key, by pointing to field 102 (on a touch screen) or the like. For the example in this description, it will be assumed that a mouse is available.

Upon clicking on field 102, this field is marked, e.g. by inverting it or changing its colour. In FIG. 17b, marking is indicated by shading 107.

Further, a secondary screen or sub-screen 108 appears on the screen, partially covering temporarily unused space or fields. Sub-screen 108 offers various alternatives for <pattern>s to be defined, namely CONTRACTION, ACCELERATION, DECELERATION, BASELINE and VARIABILITY. An <edit> field 109 allows the expert to define further <pattern>s not yet existing in the expert system.

Now let us assume that CONTRACTION has been selected as the <pattern> to be defined, by moving the cursor (with the mouse) to field 110 and clicking on that field. The label <pattern> in field 102 disappears and is replaced by "CONTRACTION", as shown in FIG. 17c. Likewise, sub-screen 108 disappears.

In the next step, the expert may click on field 103, namely <pattern type>. This field becomes shaded, and a second sub-screen 111 appears (FIG. 17d) offering various <pattern type>s of CONTRACTION for selection. It will be appreciated that the contents of the sub-screen depend on the selected <pattern>, i.e. if another <pattern> than CONTRACTION had been selected, another subscreen would appear in the second step.

Sub-screen 11 offers predefined characteristics of CONTRACTION, namely SMALL, NORMAL, HYPERSTOLIC, STRONG, OSCILLATING, TYPE 1 and TYPE 2 (TYPE 3 may also exist, but has been omitted in FIG. 17d for graphical purposes). Further, the user may define additional <pattern type>s not yet present in the expert system by using the <edit> key 112.

Assumed STRONG has been chosen as the <pattern type>, <pattern type> will be replaced by STRONG, and sub-screen 111 will disappear. The screen looks now as shown in FIG. 17e.

Next, the expert clicks on <condition> field 104, which will be shaded or highlighted (FIG. 17f). Sub-screen 113 offers now two predefined ways to define the condition:

Clicking on "CONTRACTION is" field 114 may be used to define a rule dependent on another definition of CONTRACTION, e.g. in the form "CONTRACTION is STRONG if CONTRACTION is HYPERSTOLIC". "Expression <rel> expression" field 115 may be used to define the <pattern> in dependence of certain parameters as e.g. determined by trace processor 63, and the <edit> field 116 offers the possibility to define further conditions, on request of the expert.

In the given example, field 115 has been clicked on. As shown in FIG. 17g, subscreen 113 disappears, and the <condition> field 104 (FIG. 17f) is replaced by three additional fields 117-119, labeled "expression", "<rel>" and "expression".

Fields 117–119 allow the user to define parameters ("expressions", 117 and 119) and their relation ("<rel>", 118) to each other.

If the expert clicks on field 117, the screen is modified as shown in FIG. 17h; i.e., field 117 is shaded, and sub-screen 120 appears. Said sub-screen offers certain parameters, like "Begin of contraction" (BOC). Needless to say that the appearing parameters depend on the selected <pattern>, i.e. for "<pattern>=DECELERATION", another sub-screen would appear. Like in the former steps, it is possible to define further parameters of interest with the <edit> key 121. The <edit> key may also be used to enter numeric values.

In case "AREA_A" is selected as <expression>, <expression> field 117 is replaced by "AREA_A", see FIG. 17i, reference number 122. Clicking on <rel>field 118 leads now to the screen appearance of FIG. 17k, wherein the selected <rel> field 118 is shaded, and sub-screen 123 overlays part of the screen. This sub-screen offers several mathematical or logical operators for selection, e.g. "=", ">", "#" or the like. It will be appreciated that there may be other possible operators than shown, e.g. "AND", "OR" etc.

Let us assume ">" is the relation we are looking for. We click on field 124 and obtain the screen appearance of FIG. 17l,. i.e. "<rel>" field 118 has been replaced by ">" field 125, and sub-screen 123 has disappeared. Selection of "expression" field 119 leads to the screen of FIG. 17m, wherein <expression> field 119 is shaded and sub-screen 126 is shown (actually, as we are still editing contractions, this is the same sub-screen as sub-screen 120 in FIG. 17h).

We select now "AREA_B" (reference number 127). This leads to the final screen depicted in FIG. 17n which shows the new rule we defined:

CONTRACTION is STRONG if
AREA_A>AREA_B

It will be appreciated that neither the above process of defining a rule, nor the screen appearance, nor the options offered, nor the overlay structure used, are mandatory for practising the present invention. It is also possible to add further steps to the editing process, for example, in order to define complex rules with several relations like CONTRACTION is STRONG if
(AREA_A>AREA_B) and AMPLA>=60, or to define "intermediate" rules which themselves are used as parameters in a generic rule.

The defined rule is then stored in rule memory 90 (FIG. 4). In the representation of FIG. 16, this would be pot 96 containing the classification rules.

The following table lists several useful <pattern>s, together with possible <pattern type>s, <condition>s, <expression>s and <rel>ations:

| Pattern | Pattern Type | Condition | Expression | <rel> |
|---|---|---|---|---|
| CONTRACTION | | | | |
| ACCELERATION | | | | |
| DECELERATION | | | | |
| BASELINE | | | | |
| VARIABILITY | | | | |
| <edit> | | | | |
| Contraction | SMALL | CONTRACTION is type | BOC | = |
| | NORMAL | expression <rel> expres- | EOC | > |
| | HYPERSTOLIC | sion AND/OR ... | DOC | < |
| | STRONG | <edit> | RESTING TONE | >= |
| | OSCILLATING | | AMPLC | <= |
| | TYPE 1 | | TMAXOC | # |
| | TYPE 2 | | EXTREMA | * |
| | TYPE 3 | | AREA_A | ~ |
| | <edit> | | AREA_B | |
| | | | AREA | |
| | | | PREV CONTRACT. | |
| | | | NEXT CONTRACT. | |
| | | | <edit> | |
| Acceleration | PERIODIC | ACCELERATION is type | BOA | = |
| | INITIAL | expression <rel> expres- | EOA | > |
| | COMPENSATORY | sion AND/OR ... | DOA | < |
| | SPORADIC | <edit> | AMPLA | >= |
| | <edit> | | AREA | <= |
| | | | FHR | # |
| | | | CONTRACTION | * |
| | | | CONTR:BOC | ~ |
| | | | CONTR:EOC | |
| | | | TMAXOC | |
| | | | PREV ACCEL | |
| | | | NEXT ACCEL | |
| | | | PREV DECEL | |
| | | | NEXT DECEL | |
| | | | <edit> | |
| Deceleration | PERIODIC | DECELERATION is type | BOD | = |
| | EARLY | expression <rel> expres- | EOD | > |
| | LATE | sion AND/OR ... | DOD | < |
| | VARIABLE | <edit> | RECOVERY TIME | >= |
| | LATE VARIABLE | | LATENCY TIME | <= |
| | SPORADIC | | LAG TIME | # |
| | PROLONGED | | AMPLITUDE | * |
| | <edit> | | AREA | ~ |
| | | | RESIDUAL AREA | |
| | | | SLOPE DESC | |
| | | | SLOPE ASC | |
| | | | BASELINE | |
| | | | FHR | |
| | | | CONTRACTION | |
| | | | CONTR:BOC | |
| | | | CONTR:EOC | |
| | | | TMAXOC | |

-continued

| Pattern | Pattern Type | Condition | Expression | <rel> |
|---|---|---|---|---|
| | | | PREV ACCEL | |
| | | | NEXT ACCEL | |
| | | | PREV DECEL | |
| | | | NEXT DECEL | |
| | | | <edit> | |
| Variability | SILENT A | VARIABILITY is type | FREQUENCY | = |
| | SILENT B | expression <rel> expres- | AMPLITUDE | > |
| | SILENT C | sion AND/OR ... | INTEGRAL | < |
| | UNDULATORY A | <edit> | STANDARD DEV | >= |
| | UNDULATORY B | | MEAN | <= |
| | UNDULATORY C | | <edit> | # |
| | SALTATORY A | | | * |
| | SALTATORY B | | | |
| | SALTYTORY C | | | ~ |
| | SLEEPING | | | |
| | AWAKE | | | |
| | STRESSED | | | |
| | FETAL MOVEM. | | | |
| | <edit> | | | |

As mentioned above, there is also the possibility of invoking already existing rules and to edit, i.e. modify them. One such example is the screen in FIG. 17o which would appear when key 105 ("Rules") had been pressed in FIG. 17a. In the screen depicted in FIG. 17o, the user could click on one of the displayed rules, in order to get it edited. He could then modify the existing rule in similar steps than described above, i.e. click on one of its elements, get a sub-screen containing alternate selections, and select the right one.

Returning now to the embodiment of FIG. 4, statistics processor 66 calculates several useful parameters (like mean and standard deviation) which may be invoked for trend processing, in case an alarm occurred or simply if information about longer time periods is requested. It also gets information created by other processors such as trace processor 63, stores the number and density of accelerations and decelerations, and the like. Its output is fed to statistics memory 128 for later processing, invokement or for printing on recorder 34. The kind of information collected by the statistics processor, as well as its operation and the presentation or appearance of collected data, is likewise user-configurable, as indicated by connection 129 to rule memory 90.

The next element to be discussed in the context of FIG. 4 is score processor 67 which is a major component of the present invention.

It is common use in gynecology to assess the CTG manually and "score" it. Scoring means that certain criteria are checked for presence, e.g. the level of the FHR baseline is checked whether it is below 100 bpm. In case the checked criterion is detected (e.g., baseline<100 bpm), a number (the "score"; in this example: 4) is assigned to it. Upon completion of this process, all single scores are added, thus revealing a "sum-score". The sum-score is a combined assessment of the fetal condition. In case it exceeds certain limits, this is an indication that therapy is required, e.g. change of the mother's position, oxygen therapy or even Caesarean section.

Usually, the sum-score is assigned to three different conditions of the fetus, namely "normal", "prepathologic" and "pathologic".

A typical score table listing criteria and their score is depicted in FIG. 19. The patterns evaluated in this specific score table are baseline level average, number of accelerations greater than 15 beats per minute in amplitude, number of late decelerations with amplitude >60 beats per minute, average amplitude of baseline variability in bpm, and frequency of baseline variability (taken over the last 30 minutes). One will note that, for example, a frequency of baseline variability (FHR) below 1 oscillation per minute results in three score points. Another possible score table has been published in Hammacher, Einführung in die Cardiotokographie, 2. Teil: Die Wehenmessung, Die Schweizer Hebamme, 74. Jahrgang, 1. Juni 1976, Nr. 6, which is hereby incorporated by reference.

There are several commonly used score tables, like the "Hammacher" score and the "Fischer" score, for manual evaluation of the CTG. Use of either of these score tables depends on the specific needs of a hospital, experiences in the past, and personal preference. However, it would be preferable to have a score table which even may be further adapted to the local environment of a hospital. Let us e.g. assume that, in a small hospital, a physician is not always present, in particular over night and during the weekend; instead, in case of complications during birth, he will be called by the midwife. Let us further assume that he needs 30 minutes from his home to the hospital.

In such case, he may want early alert. For example, he may want to reduce the sum-score indicating a pathological condition from 5 to 4, or he may want to assign a higher score to late decelerations (which are always a serious indication that something goes wrong).

For this purpose, the criteria in the score table, their values, the scores and the assignment of the sum-score to "normal", "prepathological" and "pathological" conditions is subject to expert control and editing, as depicted in FIG. 4 by arrow 130. In the environment of FIG. 16, processing of the score table has been drawn by "rule based score table and alarming" box 131. The rules according to which this box operates are stored in "pot" 132 which indicates the score and alarm rules. Examples of rules used for scoring and assessment are:

if <6 NORMAL CONTRACTIONS in 60 min. then
CTG is NORMAL if >2 STRONG CONTRACTIONS in 10 min. then
CTG is PREPATHOLOGIC if AOC in 10 min.>15 000 then CTG is
PATHOLOGIC (AOC=Summed Amplitudes of contractions)

Like in the preceding steps, those rules are subject to modification and editing by an expert via expert interface 74.

As expert modification of the score table is one of the key points of the present invention, one typical example of an editing process will now be described with reference to FIGS. 20a to 20d. As in the above examples, editing requires connection to an appropriate personal computer or display, in case a stand-alone monitor is used.

On the first screen depicted in FIG. 20, the "Score Editor" mode (ref. no. 133) of the expert interface offers the choice to retrieve an existing score and modify it (field 134). (The fetal monitor may contain several defined or predefined score tables which may be activated according to the application; however, it is understood that only one of the defined score tables can be active, i.e. used for CTG evaluation, at a certain point in time. The process of activating an existing score table, i.e. designating it for a specific application, is not described in detail herein). This is the easiest way of generating a user defined score table and applicable in the majority of the cases, as the expert will usually only modify one or two specific features in an existing score table, instead of defining a completely new one. However, the expert interface also offers this choice ("Define new Score" field 135). Further, an "exit" field 136 may be used to terminate editing.

In the illustrative embodiment of the present example, "Retrieve Score" may have been selected. What appears is the screen of FIG. 20b, wherein the "Retrieve Score" field 134 has been highlighted or shaded (ref. no. 137). Further, the predefined score tables, i.e. score tables already existing in the fetal monitor (cf. ref. no. 132 in FIG. 16), are offered for selection (fields 138 to 142).

Now let us assume that the expert selects editing of existing score #1. The screen depicted in FIG. 20c appears.

In this screen, line 143 indicates that the score presently defined as score #1 is the standard "Hammacher" score. The various fields offer now the following choices:
 a) edit, i.e. modify the "Hammacher" score for specific needs (field 144);
 b) select another standard score, namely "Fischer" score, "Manning" score or "Maeda" score (fields 145–147);
 c) exit editing (field 148).

Note that fields 145 to 147 will be used quite often in practice, as the expert will frequently only desire to select another standard score table, but not to perform the task of defining a completely new score, nor to even modify one of the standard scores.

However, for the purpose of illustration, let us assume he wants to modify the standard "Hammacher" score. In case field 144 is selected, the screen of FIG. 20d appears. Sub-screen 149 represents the "Hammacher" score table (for graphical purposes, the contents of the score table have not been drawn). A certain feature, limit or other characteristics of this table may now be edited by moving the cursor to the respective field and clicking on it. The feature will then be highlighted or shaded, and another screen (not shown) will offer choices, or even allow free editing, of the selected feature.

Instead, it is also possible to define a completely new feature not yet contained in the "Hammacher" score table, by clicking on "add" field 150. The expert interface will then enter an appropriate editing mode allowing the user to define a new feature, and the conditions under which it will generate scores.

Editing mode will be left, and the modified score will be stored by clicking on "exit" field 148.

By the way, the definition of a completely new score (ref. no. 135 in FIG. 20a) is performed in similar steps. A sub-screen for the features of the score table will then appear as well—however, the difference to the above example is that this form of a score table will be initially empty.

In the embodiment of the invention described herein, automatic scoring is performed any 10 minutes, taking into account the CTG and the derived patterns of the last 30 minutes (which are values haven proven valuable in clinical practice). However, the interval between subsequent assessments, and the time frame taken into account, may likewise be subject to expert modification.

It will be apparent from the above explanations that the score table is also used as some kind of "alarm table" defining the conditions under which an alarm or alert occurs. In the environment of FIG. 16, this is indicated by "lamps" 151 to 153 which represent the classification, according to the score table, as "normal" (ref. no. 151), "prepathologic" (ref. no. 152) or "pathologic" (ref. no. 153). Classification as "prepathologic" or "pathologic" may cause various steps of alerting or alarming clinical personnel.

In FIG. 4, this task is performed by alarm handler 154. In the symbolic representation of this figure, the "alarms out" output has been designated as 155. However, it will be appreciated that alarming may comprise several actions, like illuminating the red backlighting module on the front end of the fetal monitor (cf. backlighting modules 16 and 21 in FIG. 1), switching on an acoustic alarm, transmitting an alarm message to a connected central station, recording the alarm on recorder paper (ref. no. 11 in FIG. 1), or the like. Further, the selected alarm or alert will depend on the assessment (normal/prepathologic/pathologic), or directly on the score. For example, a "prepathologic" assessment will not necessarily cause an acoustic alarm.

The user of the fetal monitor has full control over the generated data. For example, he may request a score to be evaluated and printed, even out of normal order, by pressing an appropriate key or a keystroke sequence. Further, he may at any time cause the fetal monitor to print the trend information over a specific time range, the statistics, histograms etc. Of course, such is easier to perform if the fetal monitor is connected with a display or a central station equipped with a display; however, printout on an internal recorder is likewise possible.

An example is shown is FIG. 21. This is the outline of a screen appearing on the display of a central station, or the printout on an internal recorder of the fetal monitor.

The FHR real-time trace is shown as 157, and the TOCO real-time trace as 158. Shown are further: The time in 10 min. intervals (ref. no. 159), fetal movements (ref. no. 160), the "Hammacher" score (161) and the "Fischer" score (162), also in 10 min. intervals. If a colour display or recorder is used, it is further possible to depict dangerous trace segments, like the strong decelerations 163a, 163b and 163c, in different colours (e.g. red instead of black). In case of a black-white display or recorder, different thickness of the lines, dotted lines etc. may be used. Likewise, detected valid contractions in the TOCO channel (see contractions 164a, 164b and 164c) may be marked or drawn in a different colour (e.g. blue).

Upon user request (e.g. pressing a designated button or entering a keystroke sequence), the score table 165 at a certain point in time is shown as an overlay window. In the given case, a short form of the "Hammacher" score"). A third depression of the "reasoning" key presents the alarming parameters, e.g. the baseline. Fourth and fifth depression of the "reasoning" key retrieve the values of the parameters and the time of their occurrence in the trace.

A complete example of a "reasoning" list and the related levels will be given below:

| General description of level | Example | Assessment of trace | Score table | Alarming parameters | Real values of parameters | Times of occurence in trace |
|---|---|---|---|---|---|---|
| Get user's attention | Flash red lamp | | | | | |
| Main explanation | Flash red lamp | "pathol." | | | | |
| Score (level and type) | Flash red lamp | "pathol." | "g" "user score" | | | |
| Explain partitioning of score | Flash red lamp | "pathol." | "g" "user score" | BASELINE 2 DECEL. 4 VARIAB. 3 | | |
| Give reasons for part scores | Flash red lamp | "pathol." | "g" "user score" | BASELINE 2 DECEL. 4 VARIAB. 3 | >180 bpm >4/10 min <1 Osc/min | |
| Give references | Flash red lamp | "pathol." | "g" "user score" | BASELINE 2 DECEL. 4 VARIAB. 3 | >180 bpm >4/10 min <1 Osc/min | 14h00–14h30 14h20, 14h23, 14h25, 14h29 >14h20 | score table has been invoked and displayed in the window, parameters or patterns contributing to the score are shown, as well as the sum-score (6.00 in this case). Further, the clinical assessment (here: Prepathological) is given.

Further information of interest in the score table window is the time (01:10:00) and the patient's name (MUELLER). Fields 166 and 167 offer choices to CLOSE the window, i.e. make it disappear, and to request help, respectively.

The fetal monitor according to the present invention incorporates a further advantageous operating mode for supplying the user with information. This is the "reasoning" mode performed by reasoning processor 156 (FIG. 4) which will now be explained.

As will be apparent from FIG. 21, the fetal monitor displays or prints the sum-score, regardless whether any prepathological or pathological assessment, or a related alarm, occurred (it will be appreciated that it might be useful—although not shown in FIG. 21—to display or record alarms and/or alerts as well). Regardless which information is displayed or printed in case of a dangerous sum-score or an alarm or alert, it might happen that the user is interested in further detailed information on the reasons of the event. Even during normal operation, i.e. "normal" assessment of the fetal condition, he might want to know the reason for a sum-score exceeding zero.

Such may be performed by pressing a "reasoning" key on the fetal monitor or the central station. If such happens, the fetal monitor offers more qualified information on the reason of the event (by display or printout). Pressing the "reasoning" key a second time will cause the monitor to provide a deeper level of information, and so on.

As a practical example, let us assume the fetal monitor switches a red backlighting module on in case an alarm condition occurred, in order to get user attention. In case the "reasoning" key is pressed, the user will get (in a first level) the basic assessment of the trace, e.g. "pathologic". Pressing the "reasoning" key a second time will reveal the sum-score, e.g. 9, and the score table used for calculation of this score (e.g., "user It will be appreciated that the various levels of reasoning, as well as the information presented in each level, may be subject to expert modification as well.

One alternate embodiment of handling alarms and reasoning will be given now, with reference to the flowcharts in FIGS. 22a and 22b.

In case the sum-score exceeds the lower of two (adjustable) limits, e.g. 6 (reference number 168), corresponding to a prepathologic assessment, an optical alert like a red backlighting module is switched on (box 169). If an upper limit is exceeded as well (corresponding to a "pathologic" assessment)—box 170—, the optical alert is accompanied by an acoustic alarm (step 171). Subsequently, the assessment of the CTG and the calculated score are printed, see boxes 172 and 173.

The fetal monitor checks now whether the "reasoning" key has been depressed (step 174). If no, the routine jumps to the exit (ref. no. 175). If yes, the alarming parameters are printed (step 176). In case the "reasoning" key is pressed again (step 177), the real value of the parameters is printed (box 178); otherwise, operation stops. Last not least, a third depression of the "reasoning" key (step 179) causes printout of the times of their occurrence in the trace, i.e. the CTG (step 180).

It will be appreciated that reasoning may not only be performed by pressing an appropriate key, but also by other measures like moving the cursor on an appropriate field on the screen and clicking the mouse, or the like.

We claim:

1. Apparatus for evaluating a fetal condition prior to or during birth comprising
   (1.1) first detection means for detecting a fetal heart rate from a first signal indicative of said fetal heart rate and generating a fetal heart rate trace,
   (1.2) second detection means for detecting maternal labor from a second signal indicative of said maternal labor and generating a toco trace,
   (1.3) processing means for evaluating said fetal heart rate trace and said toco trace, said processing means generating quantities representative of possible diagnostic information, (1.4) rule based operating means for extracting, validating, classifying, and scoring at least one of: said quantities, derived parameters therefrom, said fetal heart rate trace and said toco trace, (1.5) rule storing means operatively connected with said rule based operating means for storing rules, (1.5.1) rule editing means (1.6) connection means for connecting said rule storing means with said rule editing means, (1.7) said rule editing means providing (1.7.1) a rule edit mode for setting up new rules or changing existing rules according to a user input, (1.7.2) a rule restore mode for restoring information on new or changed rules in said rule storing means, (1.8) wherein said rule based operating means is set up to operate according to information restored in said rule storing means from the time of restoration.

2. Apparatus according to claim 1, wherein said rule editing means provides a retrieve mode for retrieving rules or information on rules from said rule storing means.

3. Apparatus according to claim 2, wherein said rule editing means provides a modify mode for modifying said retrieved rules, wherein, in said rule restore mode, the modified rules are stored in said rule storing means.

4. Apparatus according to claim 1, wherein said rule editing means provides a definition mode for defining new rules, wherein, in said rule restore mode, modified rules are stored in said rule storing means.

5. Apparatus according to claim 1, wherein said rule editing means provides a select mode, wherein rules stored in said rule storing means are offered for selection, and information on a selected rule or rules are stored in said rule storing means.

6. Apparatus according to claim 1, wherein said rule editing means includes (6.1) a display, and (6.2) an edit control display.

7. Apparatus according to claim 1, wherein said rule storing means is a programmable, erasable memory.

8. Apparatus according to claim 1, wherein said rule based operating means includes fetal condition assessment means for calculation of a score according to rules stored in said rule storing means in dependence on at least one of: the quantities generated by said processing means, parameters derived therefrom, said fetal heart rate trace and said toco trace.

9. Apparatus according to claim 8, wherein said fetal condition assessment means assigns single scores to events observed in at least one of: said quantities, derived parameters, said fetal heart rate trace and said toco trace, according to rules stored in said rule storing means, and that a sum-score of all single scores is calculated.

10. Apparatus according to claim 9, wherein said rule storing means contains at least one set of predefined rules for assigning scores to events.

11. Apparatus according to claim 10, wherein said rule editing means provides a select mode, wherein rules stored in said rule storing means are offered for selection, and information on the selected rule or rules are stored in said rule storing means, and in said select mode, a selection is provided between at least said one set and another set of predefined rules, and the information stored in said rule storing means is information on a selected set of predefined rules.

12. Apparatus according to claim 9, further comprising an alarm handler and wherein said fetal condition assessment means, signals said alarm handler to generate an alert or an alarm if said sum-score exceeds a predefined limit.

13. Apparatus for evaluating the fetal condition prior to or during birth according to claim 9, wherein said rule based operating means include reasoning means for retrieving reasoning information upon user request said reasoning information including at least information on at least one of: a sum-score; a clinical assessment derived from said sum-score; single scores assigned to events; quantities, derived parameters, said fetal heart rate trace, said toco trace leading to said events, their values, and the time of their occurrence; explanations on the reason of an alarm; and further hints on a fetal situation.

14. Apparatus according to claim 13, wherein said reasoning means includes several operating levels, accessible by a user input, each operating level retrieving different reasoning information and wherein the reasoning information becomes more detailed from operating level to operating level.

15. Apparatus according to claim 13, wherein said reasoning means provides a display or printout of said retrieved reasoning information.

16. Apparatus according to claim 13, wherein said reasoning means includes means for activating said reasoning means only after occurrence of an alert or alarm.

17. Apparatus according to claim 1, wherein said processing means comprises time domain preprocessing means for preprocessing said fetal heart rate trace in the time domain.

18. Apparatus according to claim 17, wherein said time domain preprocessing means includes at least one of the following means:

(18.1) means for removing jumps in data values when a positive or negative jump exceeds a predefined limit, (18.2) means for removing a DC component from said fetal heart rate trace, (18.3) window means for applying a spectral leakage-reducing window to data values.

19. Apparatus for evaluating the fetal condition prior to or during birth, according to claim 17, wherein said preprocessing means include frequency transformation means for transforming a fetal heart rate trace into a calculated spectra the frequency domain.

20. Apparatus according to claim 19, further comprising filter means for filtering said calculated spectrum.

21. Apparatus according to claim 19 further comprising fetal heart rate (FHR) variability detection means said calculating a frequency of FHR variability by identification of a spectral line with a highest amplitude in a predefined region of said spectrum.

22. Apparatus according to claim 21, wherein said fetal heart rate (FHR) variability detection means includes amplitude detection means, said amplitude detection means calculating an amplitude of variability of the amplitude of a spectral line of highest amplitude in a predefined region of a spectrum, plus an amplitude of secondary spectral lines adjoining said spectral line of highest amplitude, provided said secondary spectral lines exceed or fall below predefined limits.

23. Apparatus according to claim 19, wherein said preprocessing means operates according to predefined rules stored in said rule storing means and is subject to editing by said rule editing means.

24. Apparatus according to claim 1, wherein said rule based operating means includes trace processing means for calculation of parameters from at least one of: said fetal heart rate trace, said toco trace, related spectra, and for identifying candidates for accelerations, decelerations or contractions.

25. Apparatus according to claim 24, wherein said rule based operating means includes validating means for validating possible candidates for events according to rules stored in said rule storing means.

26. Apparatus according to claim 24, wherein said rule based operating means includes classification means for classifying validated candidates for events according to rules stored in said rule storing means.

27. Apparatus according to claim 1, further comprising: statistics generating means for generation, storing and retrieval of clinically relevant statistical data from said quantities.

28. Apparatus according to claim 1, further comprising trend generating means for generation, storing and retrieval of clinically relevant time compressed trends from said quantities.

29. Method for evaluating a fetal condition prior to or during birth comprising the steps of:
(29.1) detecting a fetal heart rate,
(29.2) detecting maternal labor,
(29.3) generating quantities derived from said fetal heart rate and said maternal labor representative of possible diagnostic information,
(29.4) extracting, validating, classifying, scoring at least one of said quantities, and parameters derived therefrom, according to predefined rules stored in a rule memory,
(29.4.1) generating an alert or alarm if a calculated score exceeds a predefined limit
(29.5) employing, in conjunction with said rule memory, a rule editing means to perform at least one of: setting up new rules, changing existing rules, selecting predefined rules, selecting a set of predefined rules, and
(29.6) storing at least one of said new rules edited rules, information on selected rules and information on a set of rules in said rule memory so as to enable modified control of said generating step (29.4.1).

30. Method according to claim 29, further comprising a step of retrieving scoring information upon request if an alert or alarm occurred.

31. Method according to claim 29, for evaluating the fetal condition prior to or during birth comprising the step of detecting the fetal heart rate, by time domain preprocessing of the fetal heart rate that includes at least one of the following steps: removing jumps in data values when a positive or negative jump exceeds a predefined limit, removing a DC component from said fetal heart rate trace, applying a spectral leakage-reducing window to said data values.

32. Method according to claim 29 for evaluating the fetal condition prior to or during birth comprising the step of detecting the fetal heart rate by the step of transforming said fetal heart rate to a spectrum in the frequency domain by Fast Fourier Transformation.

33. Method according to claim 32, further comprising the step of applying a filter function to the spectrum.

34. Method according to claim 32 further comprising the step of detecting the frequency of the fetal heart rate variability from the spectrum according to the following formula:

$$f_{VAR} = \max{(F(i\Delta\omega))}|_{i=m}^{M}$$

wherein $F(i\Delta\omega)$ denotes single spectral lines, i is an index running over a predefined spectral range, and $f_{VAR}$ is a frequency of fetal heart rate variability.

35. Method according to claim 34, further comprising the step of detecting the amplitude of the fetal heart rate variability according to the following formula:

$$A_{VAR} = C * \sum_{i=m}^{M} |F(i\Delta\omega)|$$

wherein $F(i\Delta\omega)$ denotes single spectral lines, i is an index running over a predefined spectral range including a spectral line of maximum amplitude, C is a constant and $A_{VAR}$ is an amplitude of the fetal heart rate variability.

36. Method according to claim 29, further comprising the steps of
(36.1) identifying possible candidates for events,
(36.2) validating said possible candidates for events,
(36.3) classifying validated candidates.

37. Method according to claim 36 wherein said possible candidates for events include one of: accelerations, decelerations or contractions.

* * * * *

UNITED STATES PATENT AND TRADEMARK OFFICE
CERTIFICATE OF CORRECTION

PATENT NO. : 5,442,940
DATED : Aug. 22, 1995
INVENTOR(S) : Secker et al.

It is certified that error appears in the above-indentified patent and that said Letters Patent is hereby corrected as shown below:

Col. 39, line 42, before "display" insert -- for said --.

Col. 40, line 50, change "spectra" to -- spectrum --.

Col. 40, line 55, cancel "said" and insert -- for --.

Signed and Sealed this

Fifth Day of November, 1996

Attest:

BRUCE LEHMAN

*Attesting Officer*    *Commissioner of Patents and Trademarks*